United States Patent [19]

Axen

[11] 4,001,300
[45] Jan. 4, 1977

[54] 2,2-DIFLUORO-16-PHENOXY-PGF$_2$ ANALOGS

[75] Inventor: Udo F. Axen, Plainwell, Mich.
[73] Assignee: The Upjohn Company, Kalamazoo, Mich.
[22] Filed: Feb. 24, 1975
[21] Appl. No.: 552,708
[52] U.S. Cl. .................. 260/473 A; 260/468 D; 260/514 D; 260/520 B
[51] Int. Cl.$^2$ .............. C07C 65/22; C07C 61/76
[58] Field of Search .................. 260/473 A

[56] References Cited
UNITED STATES PATENTS
3,775,462   11/1973   Axen .................. 260/468 D FOREIGN PATENTS OR APPLICATIONS
747,348   3/1970   Belgium .................. 260/473 A
1,282,661   7/1972   United Kingdom .................. 260/473 A Primary Examiner—Paul J. Killos
Attorney, Agent, or Firm—Robert A. Armitage

[57] ABSTRACT

2,2-Difluoro prostaglandin E, F$_\alpha$, F$_\beta$, A, and B analogs are disclosed with intermediates and with processes for making them. These compounds differ from the prostaglandins in that they have two fluoro atoms at the C-2 position in place of the two hydrogen atoms at C-2 in the prostaglandins. These compounds are useful for a variety of pharmacological purposes, including antiulcer, inhibition of platelet aggregation, increase in nasal patency, labor induction at term, and wound healing.

58 Claims, No Drawings

2,2-DIFLUORO-16-PHENOXY-PGF₂ ANALOGS

BACKGROUND OF THE INVENTION

This invention relates to novel compositions of matter, to novel methods for producing those, and to novel chemical intermediates useful in those processes. Particularly, this invention relates to certain novel analogs of some of the known prostaglandins which differ from these known prostaglandins in that the analogs have two fluoro atoms at the C-2 positions in place of the two hydrogens.

The known prostaglandins PG's include, for example, prostaglandin $E_1$ ($PGE_1$), prostaglandin $E_2$ ($PGE_2$), prostaglandin $E_3$ ($PGE_3$), dihydroprostaglandin $E_1$ (dihydro-$PGE_1$), prostaglandin $F_{1\alpha}$ ($PGF_{1\alpha}$), prostaglandin $F_{2\alpha}$ ($PGF_{2\alpha}$), prostaglandin $F_{3\alpha}$ ($PGF_{3\alpha}$), dihydroprostaglandin $F_{1\alpha}$ (dihydro-$PGF_{1\alpha}$), prostaglandin $F_{1\beta}$ ($PGF_{1\beta}$), prostaglandin $F_{3\beta}$ ($PGF_{3\beta}$), dihydroprostaglandin $F_{1\alpha}$ (dihydro-$PGF_{1\alpha}$), prostaglandin A ($PGA_1$), prostaglandin $A_2$ ($PGA_2$), prostaglandin $A_3$ ($PGA_3$), dihydroprostaglandin $A_1$ (dihydro $PGA_1$), prostaglandin $B_1$ ($PGB_1$), prostaglandin $B_2$ ($PGB_2$), prostaglandin $B_3$ ($PGB_3$), dihydro prostaglandin $B_1$ (dihydro $PGB_1$). Each of the above-mentioned known prostaglandins is a derivative of prostanoic acid which has the following structure and atom numbering:

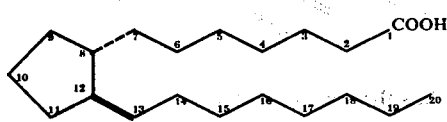

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

$PGE_1$ has the following structure:

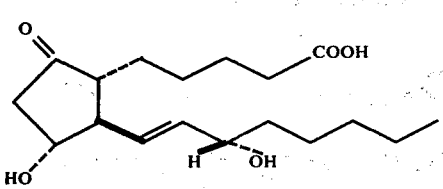

$PGE_2$ has the following structure:

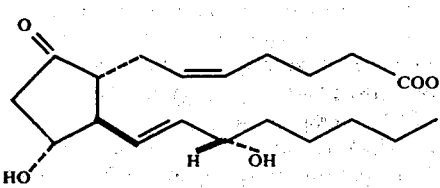

$PGE_3$ has the following structure:

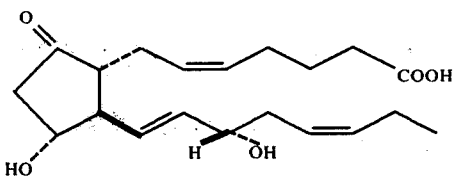

Dihydro-$PGE_1$ has the following structure:

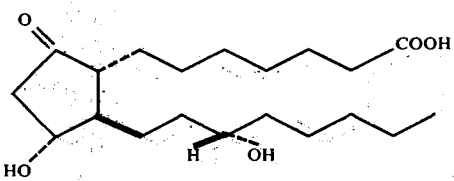

$PGF_{1\alpha}$ has the following structure:

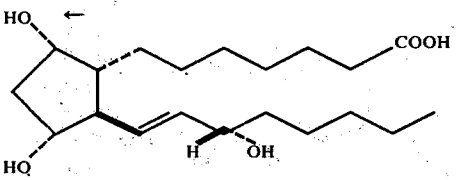

$PGF_{2\alpha}$ has the following structure:

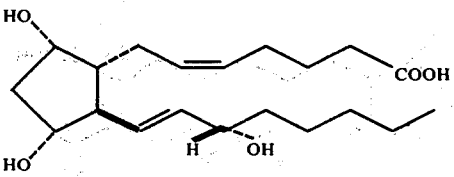

$PGF_{3\alpha}$ has the following structure:

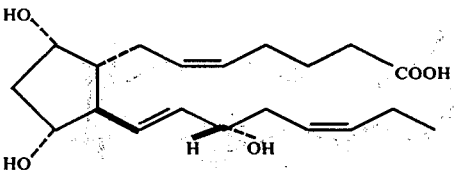

Dihydro-$PGF_{1\alpha}$ has the following structure:

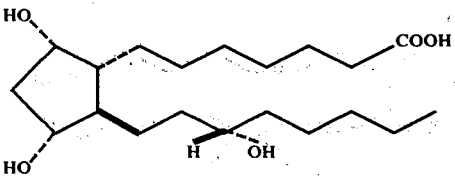

$PGF_{1\beta}$ has the following structure:

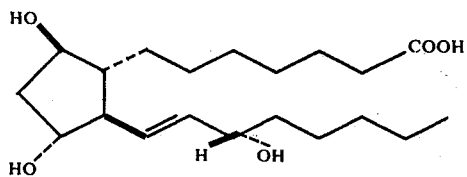

PGF$_{2\beta}$ has the following structure:

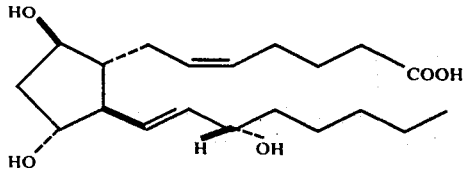

PGF$_{3\beta}$ has the following structure:

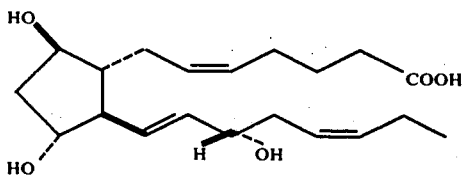

Dihydro-PGF$_{1\beta}$ has the following structure:

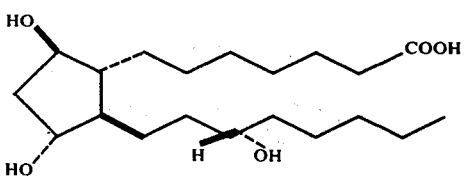

PGA$_1$ has the following structure:

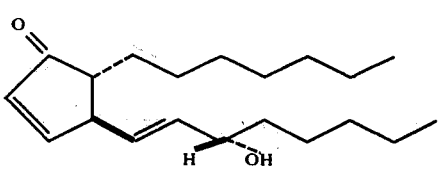

PGA$_2$ has the following structure:

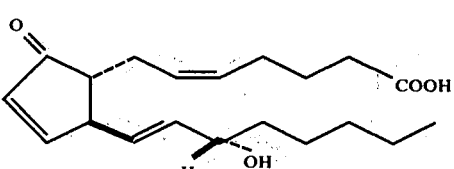

PGA$_3$ has the folllowing structure:

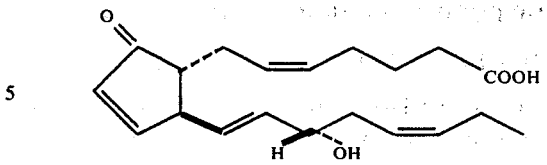

Dihydro-PGA$_1$ has the following structure:

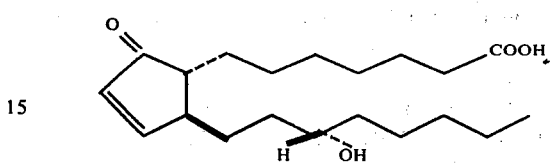

PGB$_1$ has the following structure:

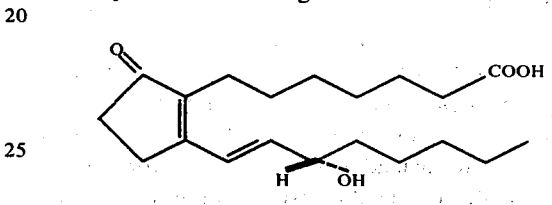

PGB$_2$ has the following structure:

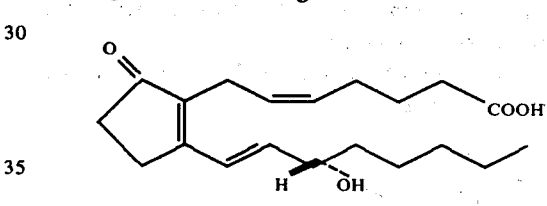

PGB$_3$ has the following structure:

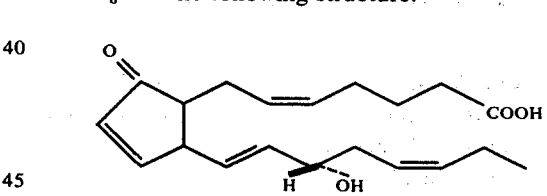

Dihydro-PGB$_1$ has the following structure:

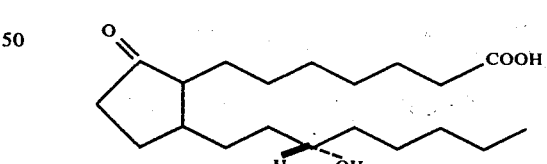

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring.

The side-chain hydroxy at C-15 in the above formulas is in S configuration. See, Nature, 212, 38 (1966) for discussion of the stereochemistry of the prostaglandins. Expressions such as C-15, and the like, refer to the carbon atom in the prostaglandin or prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e., the dextrorotatory and levorotatory forms. As drawn, the above formulas each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the terms, $PGE_1$, $PGE_2$, $PGE_3$, $PGF_{1\alpha}$, $PGF_{2\alpha}$, $PGF_{3\alpha}$, $PGF_{1\beta}$, $PGF_{2\beta}$, $PGF_{3\beta}$, $PGA_1$, $PGA_2$, $PGA_3$, $PGB_1$, $PGB_2$, $PGB_3$, and the like, refer to the optically active form of that prostaglandin with the same absolute configuration as $PGE_1$ obtained from mammalian tissues. When reference to the racemic form of one of those prostaglandins is intended, the word "racemic" or "dl" will precede the prostaglandin name.

$PGE_1$, $PGE_2$, $PGE_3$, dihydro-$PGE_1$, $PGF_{1\alpha}$, $PGF_{2\alpha}$, $PGF_{3\alpha}$, dihydro-$PGF_{3\alpha}$, $PGF_{1\beta}$, $PGF_{2\beta}$, $PGF_{3\beta}$, dihydro-$PGF_{1\beta}$, $PGA_1$, $PGA_2$, $PGA_3$, dihydro-$PGA_1$, $PGB_1$, $PGB_2$, $PGB_3$, and dihydro-$PGB_1$ and their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein. A few of those biological responses are systemic blood pressure lowering in the case of the PGE and PGA compounds as measured, for example, in anesthetized (pentobarbital sodium) pentolinium-treated rats with indwelling aortic and right heart cannulas; stimulation of smooth muscle as shown, for example, by tests on strips on guinea pig ileum, rabbit duodenum, or gerbil colon; potentiation of other smooth muscle stimulants; lipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments. Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application.

The PGE, $PGF_\alpha$, $PGF_\beta$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other antiasthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF_\alpha$, and $PGF_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, $PGF_\alpha$, and $PGF_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessesl and portions of the circulation apparatus. This blocking is avoided by the presence of these compounds. For this purpose, the compound is added gradually or in single or multiple portions to the circulating blood, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, a PGE compound, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE and PGA compounds are useful as hypotensive agents to reduce blood pressure in mammals, including man. For this purpose, the compounds are administered by intravenous infusion at the rate about 0.01 to about 50 μg. per kg. of body weight per minute or in single or multiple doses of about 25 to 500 μg. per kg. of body weight total per day.

The PGE, $PGF_\alpha$, and $PGF_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, $PGF_\alpha$, and $PGF_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose the PG compound, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first or second trimester of the normal mammalian gestation period.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered locally or systemically.

$PGE_2$, for example, is administered orally or vaginally at doses of about 5 to 20 mg. per treatment of an adult female human, with from one to five treatments per 24 hour period. $PGE_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 μg. per kg. of body weight or by intravenous infusion at a dose in the range 0.01 to 20 μg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, useful domestic animals, pets, zoological specimens, and laboratory animals. For that reason, these these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 $\mu$g/ml. of the PGE compound. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

The PGE, PGF$_\alpha$, PGF$_\beta$, PGA, and PGB compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including PGE$_1$, PGE$_2$, PGE$_3$, 13,14-dihydro-PGE$_1$, and the corresponding 11-deoxy-PGE and PGA compounds. PG compounds are useful, for example, in reducing the undesirable gastrointestinal effects resulting from systemic administration of indomethacin, phenylbutazone, and aspirin. These are substances specifically mentioned in Partridge, et al. as non-steroidal anti-inflammatory agents. But these are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex, and medical condition of the mammal, that nature and dosage regimen of the anti-inflammatory synthetase inhibitor being administered to the mammal, the sensitivity of the particular individual mammal to the particular synthetase inhibitor with regard to gastrointestinal effects, and the particular PG-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

Several compounds related to the novel compounds of this invention are known in the art. For example, 2,2- or 3,3-difluoro PGE$_1$, PGF$_1$, and PGA$_1$ are disclosed in U.S. Pat. No. 3,767,695.

SUMMARY OF THE INVENTION

This invention provides novel prostaglandin analogs, esters of said analogs, and pharmacologically acceptable salts of said analogs. This invention further provides novel intermediates useful in producing these compounds. This invention further provides novel processes for preparing these compounds.

Examples of the novel prostaglandin-type compounds of this invention can be represented by the formulas:

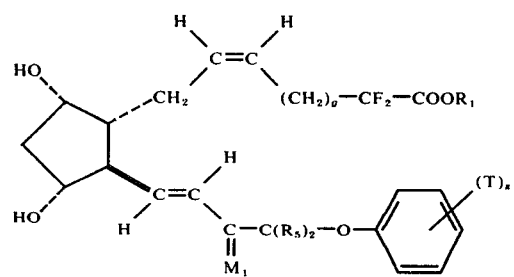
I
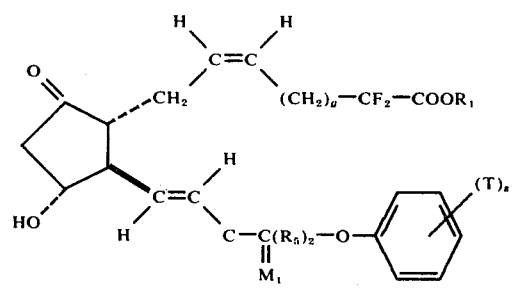
II
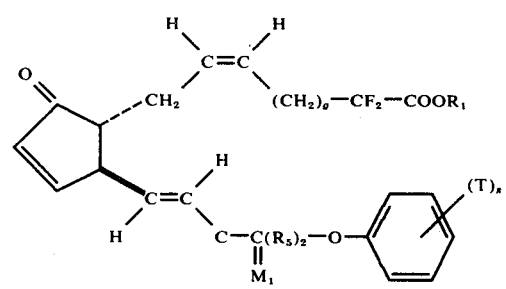
III
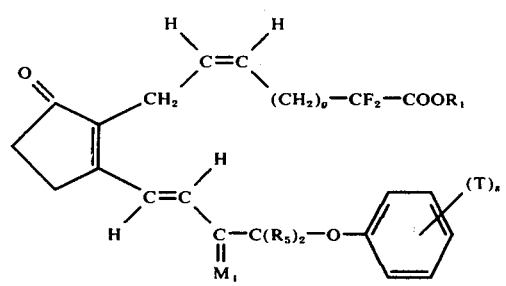
IV
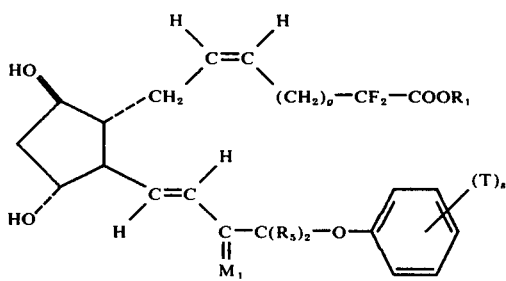
V
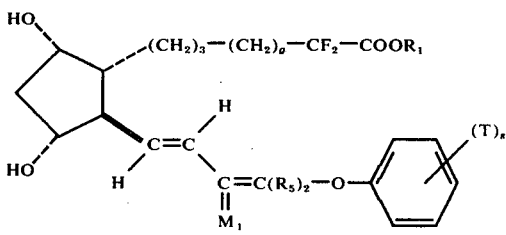
VI -continued
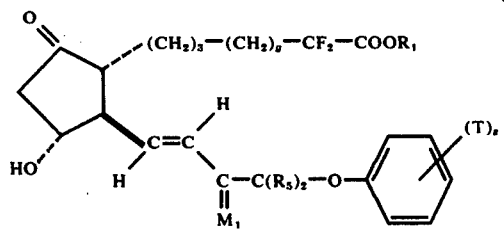 VII
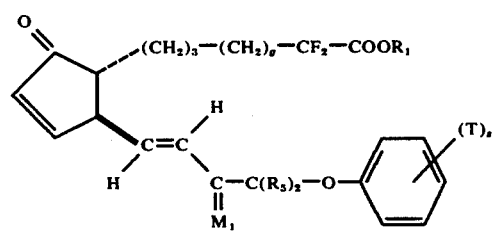 VIII
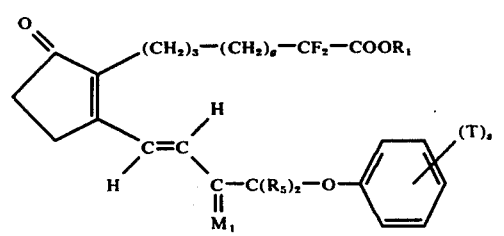 IX
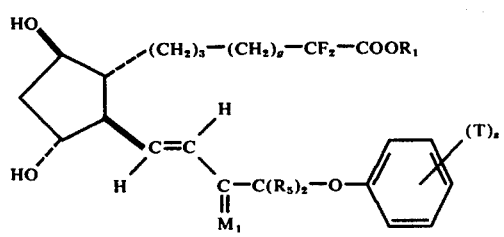 X
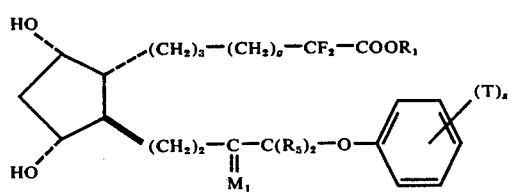 XI
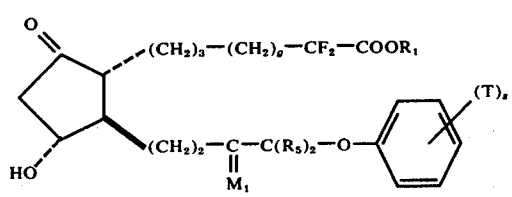 XII
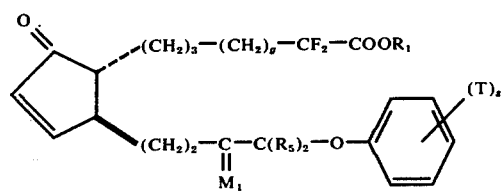 XIII
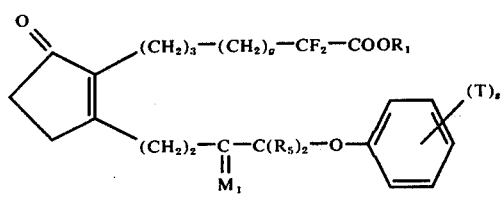 XIV -continued
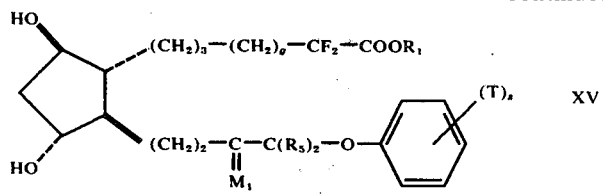
XV
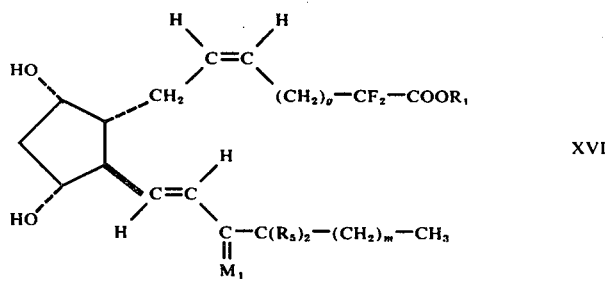
XVI
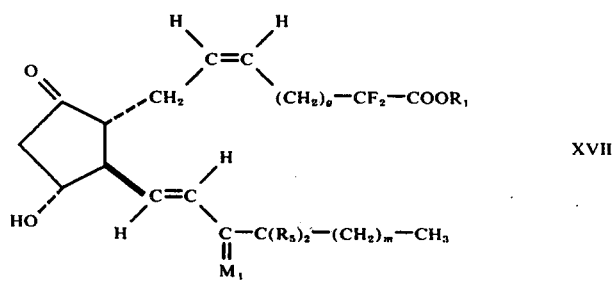
XVII
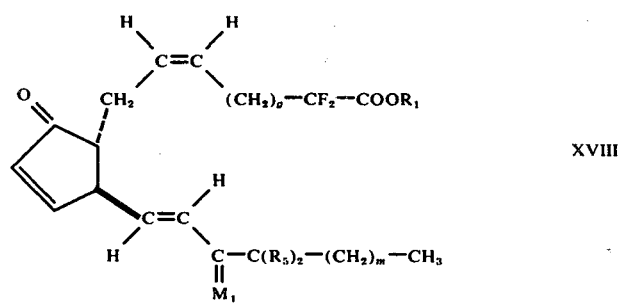
XVIII
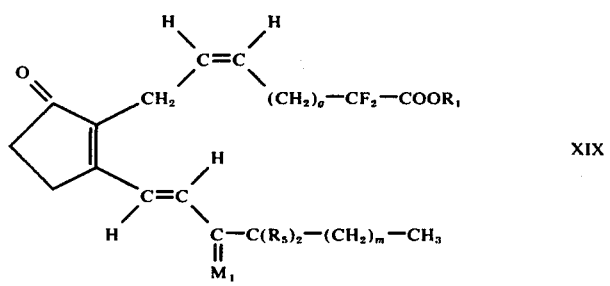
XIX
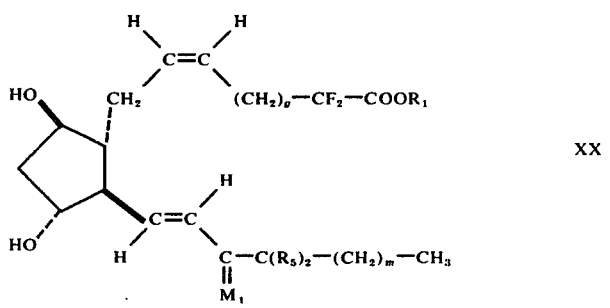
XX -continued
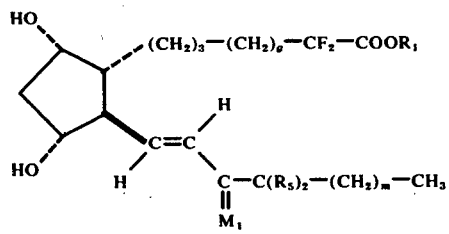
XXI
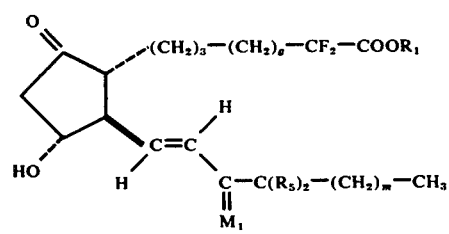
XXII
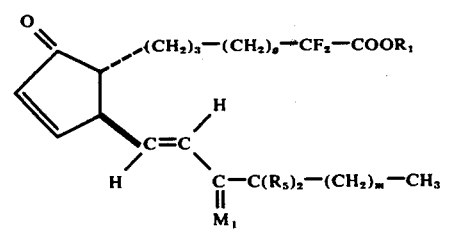
XXIII
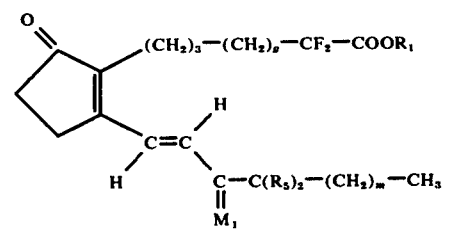
XXIV
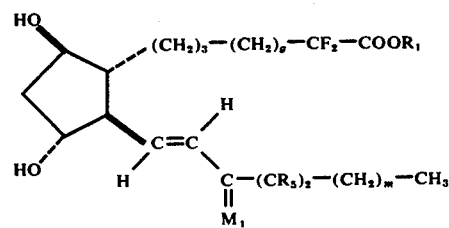
XXV
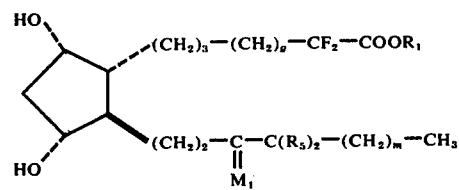
XXVI
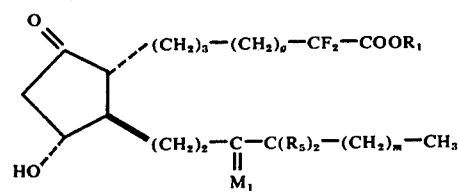
XXVII
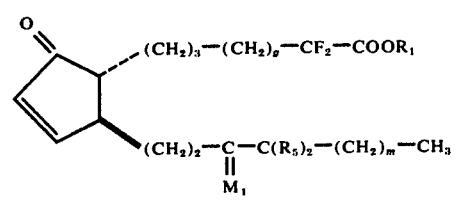
XXVIII -continued
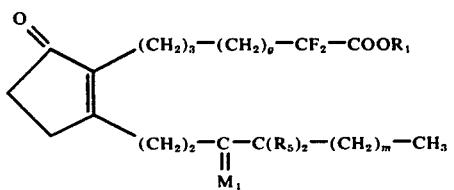
XXIX
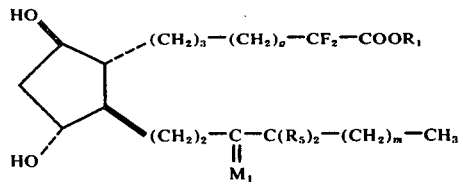
XXX
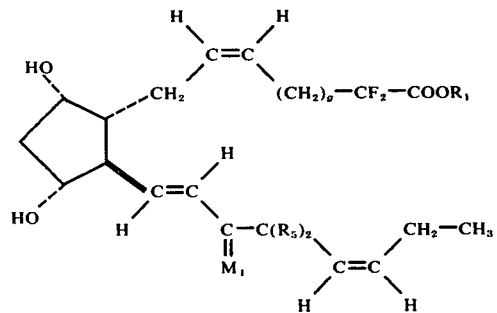
XXXI
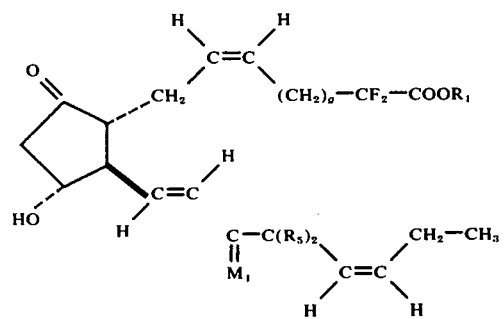
XXXII
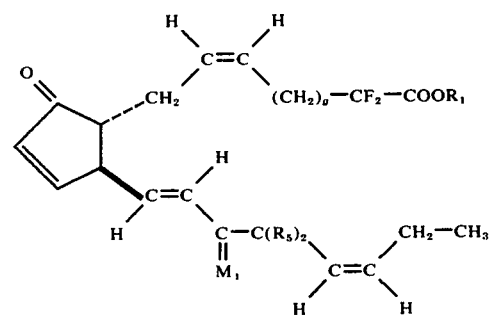
XXXIII
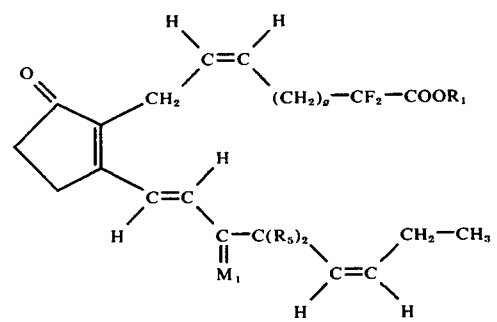
XXXIV

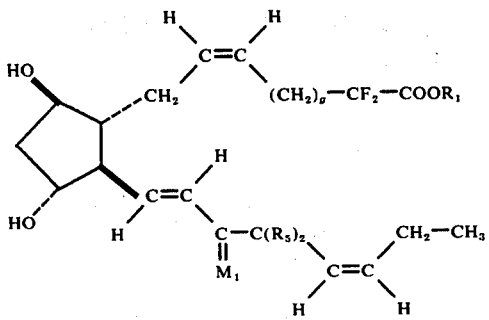

XXXV

In formulas I-XXXV g is an integer from 2 to 4, $M_1$ is

or

wherein $R_7$ and $R_8$ are hydrogen or methyl with the proviso that one or $R_7$ or $R_8$ is methyl only when the other is hydrogen; $R_1$ is selected from the group consisting of $R_2$ and $R_3$, wherein $R_2$ is hydrogen alkyl of 1 to 12 carbon atoms, inclusive, cycloalkyl of 3 to 10 carbon atoms, inclusive, aralkyl of 7 to 12 carbon atoms, inclusive, or phenyl, phenyl substituted with 1, 2, or 3 chloro or alkyl of 1 to 4 carbon atoms, inclusive, or a pharmacologically acceptable cation, and wherein $R_3$ is

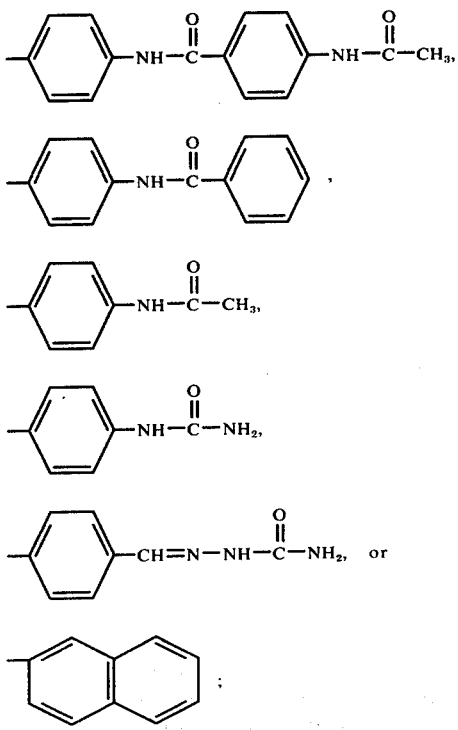

and m is an integer from 2 to 4, inclusive.

In formulas I-XV, T is alkyl of 1 to 3 carbon atoms, inclusive, fluoro, chloro, trifluoromethyl, or $-OR_{16}$, wherein $R_{16}$ is alkyl of 1 to 3 carbon atoms, inclusive, and s is 0, 1, 2, or 3, with the proviso that not more than two T's are other than alkyl; and $R_5$ is hydrogen or methyl with the proviso that $R_5$ is methyl only when $R_7$ and $R_8$ are both hydrogen.

In formulas XVI-XXX $R_5$ is hydrogen, methyl, or fluoro; with the proviso that $R_5$ is methyl only when $R_7$ and $R_8$ are both hydrogen, and with the proviso that $R_5$ is hydrogen, only when one or $R_7$ or $R_8$ is methyl. In formulas XXI-XXXV $R_5$ is hydrogen, methyl, or fluoro, with the proviso that $R_5$ is fluoro only when $R_7$ and $R_8$ are both hydrogen and with the proviso that $R_5$ is methyl only when $R_7$ and $R_8$ are both hydrogen.

In the name of the above compounds, "18,19,20-trinor" indicates the absence of 3 carbon atoms from the hydroxy or methoxy substituted side chain of the prostaglandin structure. Similarly, "17,18,19,20-tetranor" indicates the absence of 4 carbon atoms from the hydroxy or methoxy substituted side chain of the prostaglandin structure, Following the atom numbering of the prostanoic structure, C-18, C-19, and C-20 are construed as missing and the methylene at C-17 is replaced with the terminal methyl group on these 18,19,20-trinor compounds. Thus, the words nor, dinor, trinor, tetranor, and the like are construed as indicating the absence of 1, 2, 3, 4, or more carbon atoms from the designated carbon atom positions of the prostanoic acid skeleton. In naming the above compounds, "2a,2b-dihomo" indicates that two additional carbon atoms in the carboxy terminated side chain are inserted, specifically between the C-2 and C-3 positions. There are therefore 9 carbon atoms in this side chain instead of the normal 7 of the prostanoic acid structure. From the carboxy portion of this side chain, counting in the direction toward the cyclopentane ring, these carbon atoms are respectively identified as C-1, C-2, C-2a, C-2b, C-4, C-5, et cetera. The novel compounds of this invention are all substituted at the C-2 position with two fluoro groups in place of the two hydrogens. Thus, the name each of the novel compounds of this invention includes "2,2-difluoro". Also included in this invention are compounds substituted at C-16 with two fluoro groups. The name of each of these compounds includes "2,2,16,16-tetrafluoro". Also provided in this invention, are certain "16-phenoxy" and "16,16-dimethyl" compounds whose names, in similar fashion, reflect substitution at C-16.

Also, the novel compounds of this invention include compounds substituted at C-15 position with a methyl group in place of the C-15 hydrogen, or a methoxy group in place of the 15-hydroxy. The name of each of the compounds so substituted includes respectively either "15-methyl" or "15-methyl ether".

Finally, in each of the formulas above $M_1$ is either

i.e., wherein the hydroxy or methoxy is attached to side chain in the alpha configuration, or

wherein the hydroxy or methoxy is attached to the side chain in the beta configuration. The alpha configuration, specified above, represents the epimeric configuration of the hydroxy or methoxy which corresponds to the same absolute configuration as the hydroxy of $PGE_1$ as obtained from mammalian tissue.

The 15-epimer compounds, wherein $M_1$ is

will herein be named as "15-epi" compounds. Those compounds with the same absolute configuration of the hydroxy or methoxy at C-15 as in $PGE_1$ obtained from mammalian tissues are named herein without special designation of this stereochemical feature.

Each of the formulas above plus its mirror image describes a racemic compound within the scope of this invention. For convenience hereafter, such a racemic compound is designated with the prefix "racemic" or "dl" before its name. When the prefix is absent, the name is that of the optically active compound represented by the appropriate formula I-XXXV.

Examples of alkyl of to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tertbutylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,4-dimethylphenyl, 4-chloro-2-methylphenyl, and 2,4-dichloro-3-methylphenyl.

Examples of

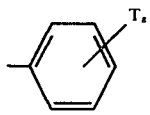

wherein T is alkyl of one to 3 carbon atoms, inclusive, fluoro, chloro, trifluoromethyl, or $-OR_{16}$ wherein $R_{16}$ is alkyl of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)chloro-2-fluorophenyl, α, α, α-trifluoro-(o-, m-, or p-)tolyl, (o-, m-, or p-)methoxyphenyl, (o-, m-, or p-)ethoxyphenyl, (4- or 5-)chloro-2-methoxyphenyl, and 2,4-dichloro(5- or 6-)methoxyphenyl.

Accordingly there is provided by this invention a compound of the formula

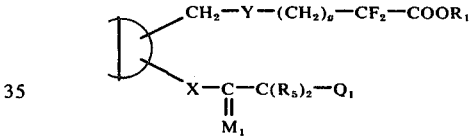

wherein g is 2 to 4, inclusive;
wherein $M_1$ is

or

wherein $R_7$ and $R_8$ are hydrogen or methyl, with the proviso that one of $R_7$ or $R_8$ is methyl only when the other is hydrogen:
wherein $Q_1$ is $-(CH_2)_m-CH_3$, wherein m is 2 to 4, inclusive, cis-CH=CH-$CH_2$-$CH_3$, or

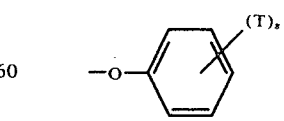

wherein T is alkyl of one to 3 carbon atoms, inclusive, fluoro, chloro, trifluoromethyl, or $-OR_4$ wherein $R_4$ is alkyl of one to 3 carbon atoms, inclusive, and wherein s is zero, one, 2, or 3, with the proviso that not more than two T's are other than alkyl; with the proviso that $Q_1$ is cis $-CH=CH-CH_2-CH_3$ only when Y is cis-$CH=CH-$;

wherein $R_1$ is hydrogen, alkyl of one to 12 carbon atoms, inclusive; cycloalkyl of 3 to 10 carbon atoms, inclusive; aralkyl of 7 to 12 carbon atoms, inclusive, phenyl, phenyl substituted with one, 2, or 3 chloro alkyl of one to 4 carbon atoms inclusive, or a pharmacologically acceptable cation,

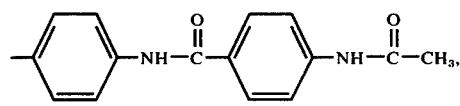

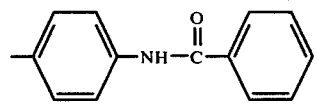

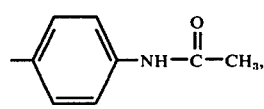

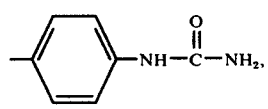

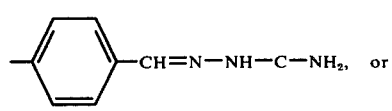

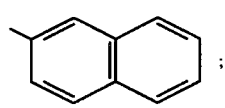

wherein $R_5$ is hydrogen, methyl, or fluoro with the proviso that $R_5$ is fluoro only when $Q_1$ is cis-$CH=CH-CH_2-CH_3$ or $(CH_2)_m-CH_3$, wherein m is as defined above, and $R_7$ and $R_8$ are both hydrogen, with the proviso that $R_5$ is methyl only when $R_7$ and $R_8$ are both hydrogen, and with the proviso that $R_5$ is hydrogen only when either one $R_7$ and $R_8$ is methyl or $Q_1$ is cis-$CH=CH-CH_2-CH_3$ or

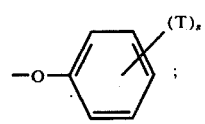

wherein X is trans-$CH=CH-$ or $-CH_2CH_2-$ and Y is $-CH_2CH_2-$, or X is trans-$CH=CH-$ and Y is cis-$CH=CH-$; wherein D is

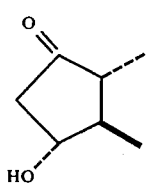

-continued

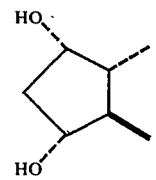

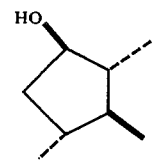

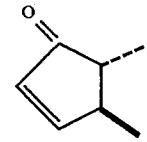

or

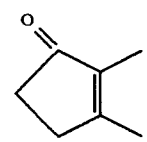

The preceeding formula, which is written in generic form for convenience, represents PGE-type compounds when D is

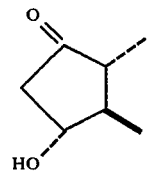

PGFα -type compounds when D is

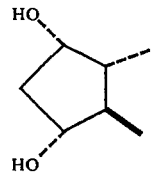

PGFβ -type compounds when D is

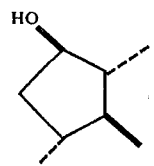

PGA-type compounds when D is

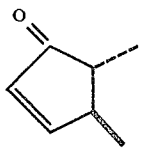

PGB-type compounds when D is

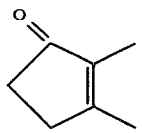

The novel compounds of this invention each cause the biological response described above for the corresponding PGE, PGF$_\alpha$, PGF$_\beta$, PGA, and PGB compounds, respectively, and each of these novel compounds is accordingly useful for the above-described corresponding purposes, and is used for those purposes in the same manner as described above.

The known PGE, PGF$_\alpha$, PGF$_\beta$, PGA, and PGB compounds are all potent in causing multiple biological responses even at low doses. For example, PGE$_1$ and PGE$_2$ both cause vasodepression and smooth muscle stimulation at the same time they exert antilipolytic activity. Moreover, for many applications, these known prostaglandins have an inconveniently short duration of biological activity. In striking contrast, the novel prostaglandin analogs of this invention are substantially more specific with regard to potency in causing prostaglandin-like biological responses, and have a substantially longer duration of biolgical activity. Therefore, each of these novel prsotaglandin analogs is surprisingly and unexpectedly more useful than one of the corresponding above-mentioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

Another advantage of the novel compounds of this invention, especially the preferred compounds defined hereinbelow, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

As discussed above, the novel compounds of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred.

For that purpose, it is preferred because of increased water solubility that R$_1$ in the novel compounds of this invention be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The novel PG analogs of this invention are used for the purposes described above in the free acid form, in ester form, in pharmacologically acceptable salt form. When the ester form is used, the ester is any of those within the above definition of R$_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal. When R$_1$ is not alkyl it is especially preferred that R$_1$ be one of the esters of the group represented by R$_3$, that is:

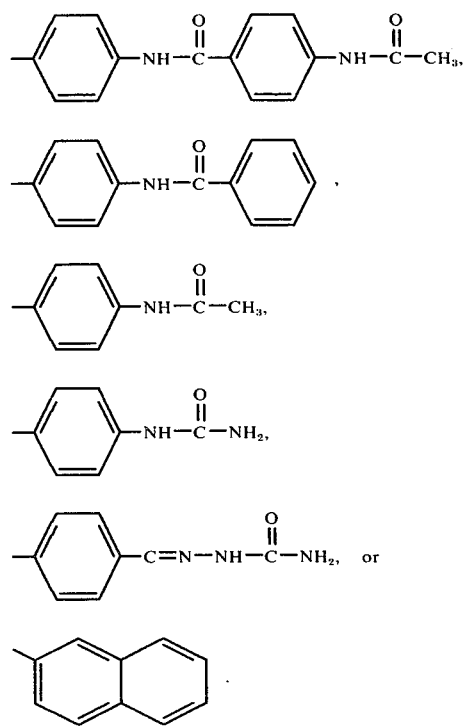

Pharmacologically acceptable salts of the novel PG analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium although cationic forms of other metals, e.g., aluminu, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methyl piperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and tri-ethanolamine, ethyldiethanolamine, N-butylehtanolamine, 2-amino-1-butanol, 2-amino-2-ethyl-1,3-propanediol, 2-amino-2-methyl-1-propanol, tris(hydroxymethyl)-aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The novel PG analogs of this invention used for the purposes described above in free hydroxy form or also in the form wherein the hydroxy moieties are transformed to lower alkanoate moieties, e.g., -OH to -OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

To obtain the optimum combination of biological response specificity, potency, and duration of activity, certain compounds within the scope of this invention are preferred.

It is preferred that the hydroxyl at C-15 be in the alpha configuration.

It is preferred that the carboxy-terminated side chain contain 7 or 9 carbon atoms. It is especially preferred that it contain 7 carbon atoms.

It is preferred that for the phenoxy or substituted phenoxy compounds of this invention that the phenyl ring have zero or one substitution, and that this substitution be selected from the group consisting of chloro, fluoro, and trifluoromethyl.

It is also preferred that the methyl-terminated side chain contain 8 carbon atoms;

The novel PG-type compounds of this invention are prepared by the methods and procedures set forth hereinbelow and in Charts A-E. With respect to Charts A-E, R$_1$ is selected from the group consisting of R$_2$ and R$_3$, wherein R$_2$ is hydrogen, alkyl of 1–12 carbon atoms, inclusive, cycloalkyl of 3 to 10 carbon atoms, inclusive, aralkyl of 7 to 12 carbon atoms, inclusive, phenyl, phenyl substituted with 1, 2, or 3 chloro, fluoro, or alkyl of 1 to 4 carbon atoms, and pharmacologically acceptable cation, inclusive, and R$_3$ is

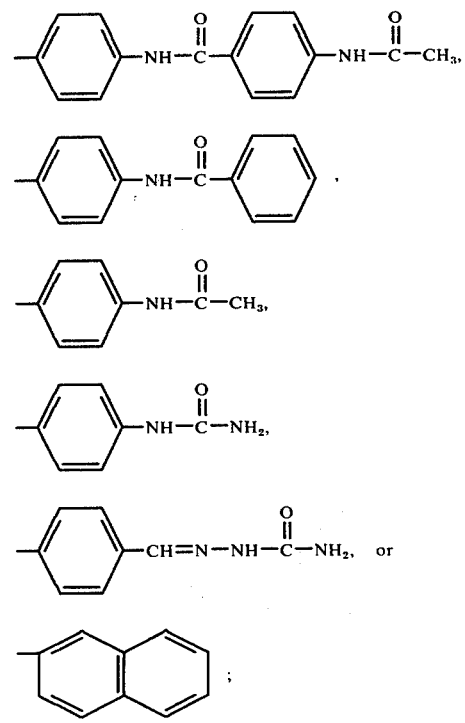

Chart A

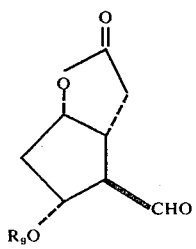

XXXVI

Chart A
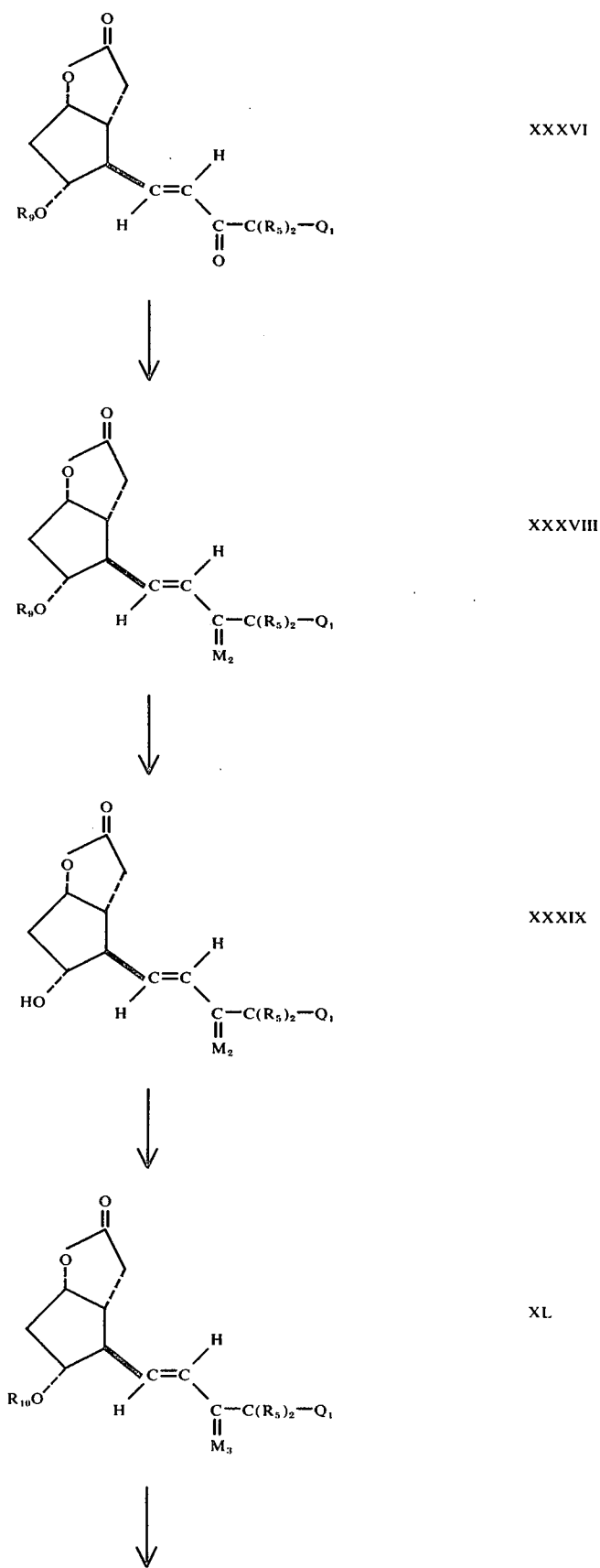
XXXVI
XXXVIII
XXXIX
XL

Chart A
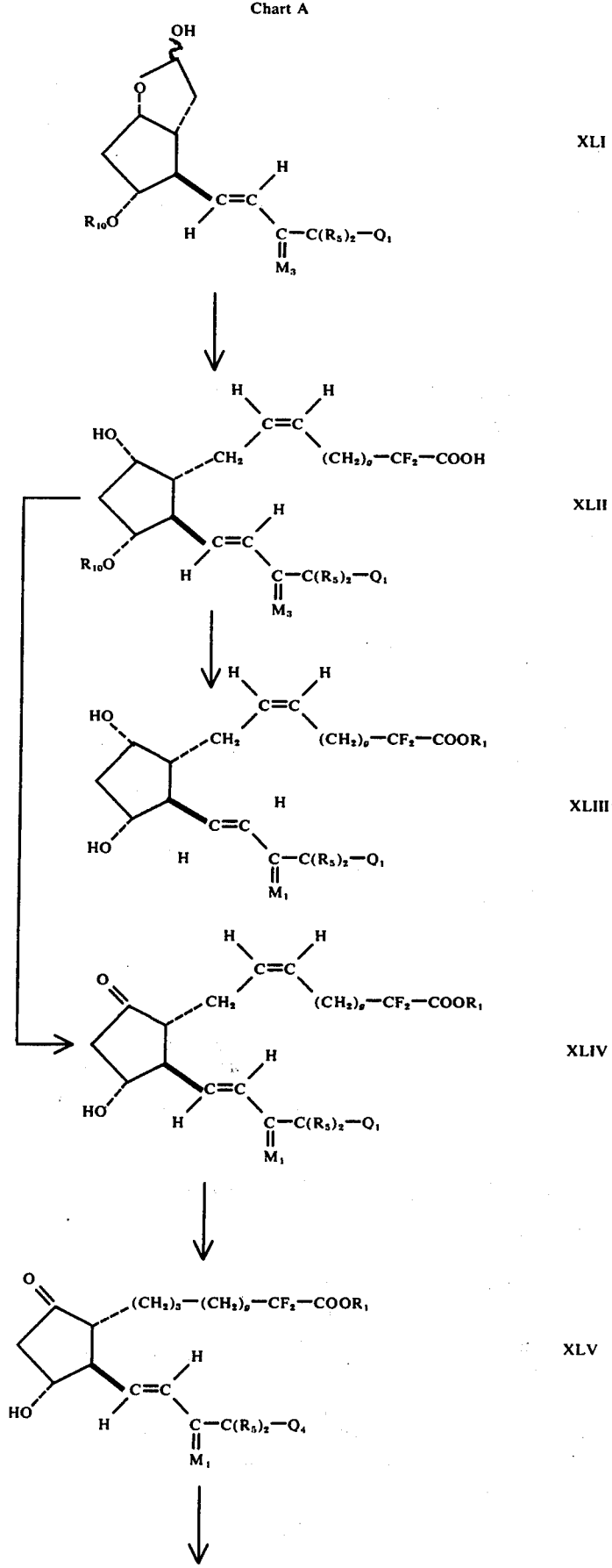
XLI
XLII
XLIII
XLIV
XLV

Chart A
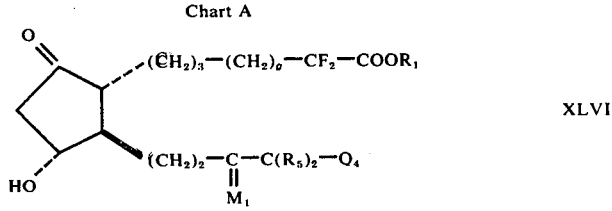
XLVI
Chart B
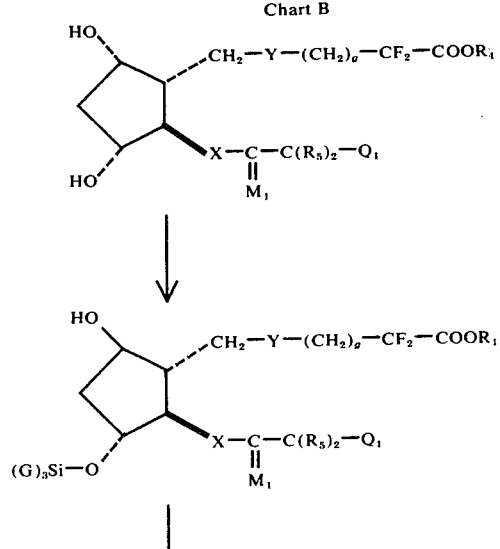
XLVII
XLVIII
-continued
Chart B
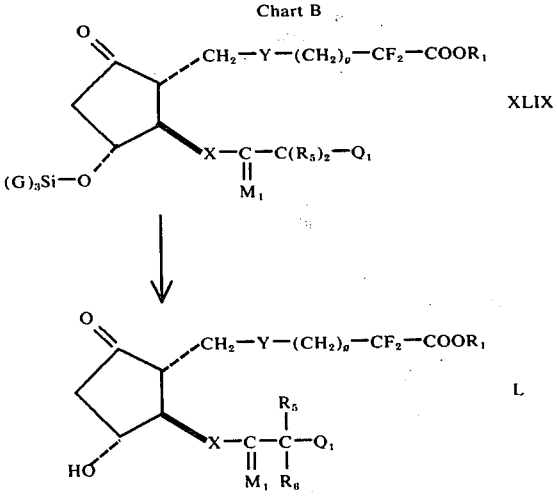
XLIX
L 4,001,300
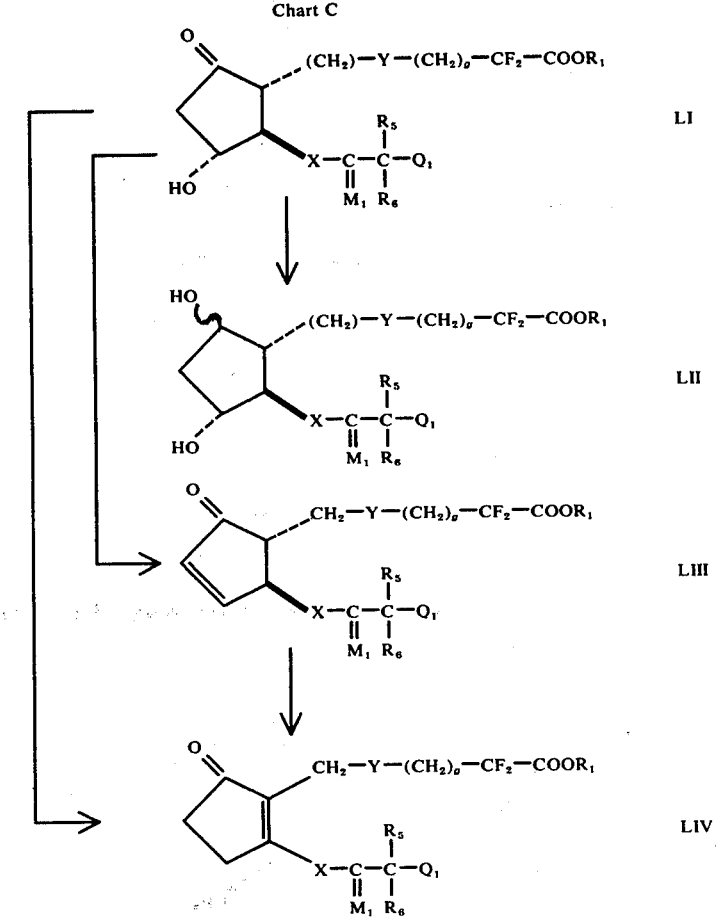
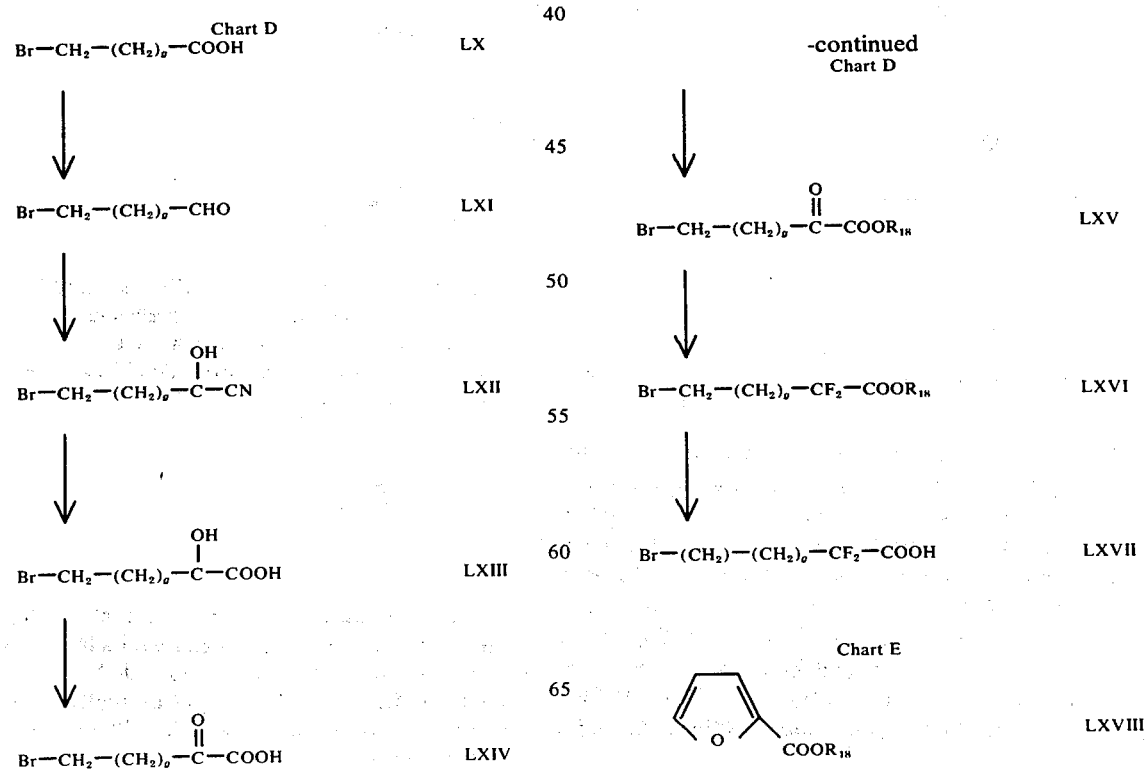

-continued
Chart E

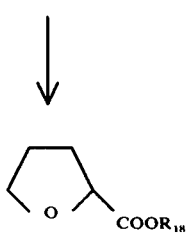  LXIX

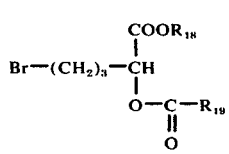  LXX

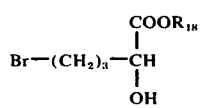  LXXI

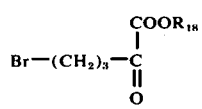  LXXII

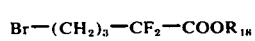  LXXIII

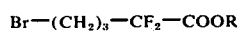  LXXIV $R_5$ is as defined above; $R_9$ is an acyl protecting group; $R_{10}$ is a blocking group; $R_{18}$ and $R_{19}$ are alkyl of 1 to 4 carbon atoms, inclusive; G is alkyl of 1 to 4 carbon atoms, inclusive, aralkyl of 7 to 12 carbon atoms, inclusive, phenyl or phenyl substituted with 1 or 2 fluoro, chloro, or alkyl of 1 to 4 carbon atoms, inclusive, with the proviso that the various G's of the Si-(G)$_3$ moiety may be the same or different; X is trans-CH=CH- and Y is either cis-CH=CH- or -CH$_2$CH$_2$- or X is -CH$_2$CH$_2$- and Y is -CH$_2$CH$_2$-; $Q_1$ and m are as defined above; $M_1$ is either

or

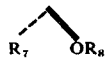

wherein $R_7$ and $R_8$ are as defined above; $M_2$ is a mixture of

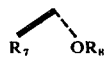

and

wherein $R_7$ and $R_8$ are as defined above; $M_3$ is a mixture of

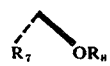

and

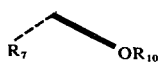

when $R_8$ is methyl, and a mixture of

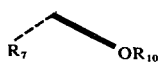

and

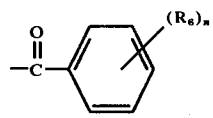

when $R_8$ is hydrogen wherein $R_7$, $R_8$, and $R_{10}$ are as defined above; and g is 2 to 4, inclusive.

Acyl protecting groups known in the art may be advantageously used in this invention. These acyl protecting groups include

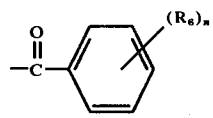  (1)

wherein $R_6$ is alkyl of one ot 4 carbon atoms, inclusive, phenylalkyl of 7 to 10 carbon atoms, inclusive, or nitro, and n is zero to 5, inclusive, provided that not more than two $R_6$'s are other than alkyl, and that the total number of carbon atoms in the $R_6$'s does not exceed 10 carbon atoms;

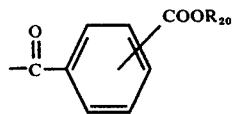

(2)

wherein $R_{20}$ is alkyl of one to 4 carbon atoms, inclusive;

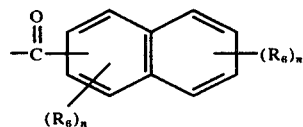

(3)

wherein $R_6$ and n are as defined above; or (4) acetyl. The bicyclic lactone aldehyde

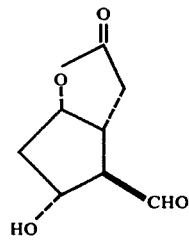

is known in the art and is available in both optically active form of preparation of optically-active products, or racemic form for preparation of racemic products.

The formula XXXVI compound may be prepared by replacing the hydrogen of the hydroxy group of the bicyclic lactone aldehyde above with the acyl protecting group $R_9$, using methods known in the art. Thus, an aromatic acid of the formula $R_9OH$, wherein $R_9$ is as defined above, for example benzoic acid, is reacted with the free hydroxy compound in the presence of a dehydrating agent, e.g. sulfuric acid, zinc chloride, or phosphoryl chloride; or an anhydride of the aromatic acid of the formula $(R_9)_2O$, for example benzoic anhydride, is used.

Preferably, however, an acyl halide, e.g. $R_9Cl$, for example benzoyl chloride, is reacted with the free hydroxy compound in the presence of a hydrogen chloride-scavenger, e.g. a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess.

As examples of $R_9$, the following are available as acids ($R_9OH$), anhydrides (($R_9)_2O$), or acyl chlorides ($R_9Cl$): benzoyl; substituted benzoyl, e.g. (2-, 3-, or 4-)-methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)toluyl, (2-, 3-, or 4-)phenethylbenzoyl, 2-, 3-, or 4-nitrobenzoyl, (2,4-, 2,5-, or 3,5-)dinitrobenzoyl, 3,4-dimethyl-2-nitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

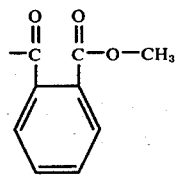

isophthaloyl, e.g.

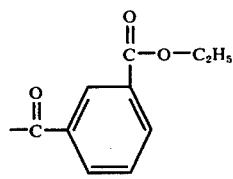

or terephthaloyl, e.g.

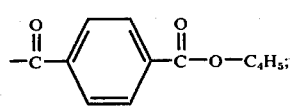

(1- or 2-)naphthoyl; substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)nitro-1-naphthoyl, 4,5-dinitor-1-naphthoyl, (30, 4-, 6-, 7-, or 8-)methyl-1-naphthoyl, 4-ethyl-2-naphthoyl, and (5- or 8-)nitro-2-naphthoyl; and acetyl. There may be employed, therefore, benzoyl chloride, and the like, i.e., $R_9Cl$ compounds corresponding to the above $R_9$ groups. If the acyl chloride is not available, it is made from the corresponding acid and phosphorus pentachloride as is known in the art. It is preferred that the $R_9OH$, $(R_9)_2O$, or $R_9Cl$ reactant does not have bulky, hindering substituents, e.g. tert-butyl, on both of the ring carbon atoms adjacent to the carbonyl attaching-site.

The formula-XXXVII compound is prepared from the formula XXXVI compound by Wittig alkylation using a phosphonate of the formula

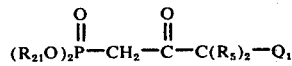

wherein $R_5$ is $Q_1$ are as defined above, $R_{21}$ is alkyl of 1 to 8 carbon atoms, inclusive. Using the sodio derivative of the above phosphonate, the trans-enone lactone is obtained stereospecifically. See D. H. Wadsworth, et al. Journal of Organic Chemistry, 30: 680 (1965).

The above phenoxy and substituted-phenoxy phosphonates are prepared by methods known in the art. See Wadsworth et al., reference cited above. Conveniently, the appropriate aliphatic acid ester is condensed with the anion of dimethyl methylphosphonate produced by n-butyllithium. For this purpose, acids of the general formula

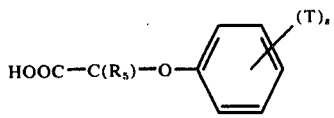

are used in the form of their lower alkyl esters, preferably methyl or ethyl. The methyl esters, for example, are readily formed from the acids by reaction with diazomethane. These aliphatic acids with phenoxy or substituted-phenoxy substitution wherein $Q_1$ is

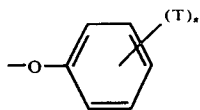

wherein T and s are as defined above, are known in the art or can be prepared by methods known in the art.

Many phenoxy-substituted acids are readily available, e.g. wherein $R_5$ is hydrogen: phenoxy-, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)chlorophenoxy-, 4-fluoro-2,5-xylyloxy-, (o-, m-, or p-)fluorophenoxy-, (2,3-, 2,4-, 2,5-, 2,6-, 3,4-, or 3,5-)dichlorophenoxy-, $\alpha$, $\alpha$, $\alpha$-trifluoro-(o-, m-, or p-)-tolyloxy-, or (o-, m-, or p-(methoxyphenoxyacetic acid; wherein $R_5$ is methyl: 2-methyl-2-phenoxy-, 2-[(o-, m-, or p-)chlorophenoxy]-2-methyl-, or 2-[(2,3-, 2,4-, 2,5-, 2,6-, 3,4-, or 3,5-)dichlorophenoxy]-2-methylpropionic acid.

Other phenoxy substituted acids are available by methods known in the art, for example, by the Williamson synthesis of ethers using an alpha-halo aliphatic acid or ester with sodium phenoxide or a substituted sodium phenoxide. Thus, the methyl ester of 2-(o-methoxyphenoxy)-2-methylbutyric acid is obtained by the following reaction:

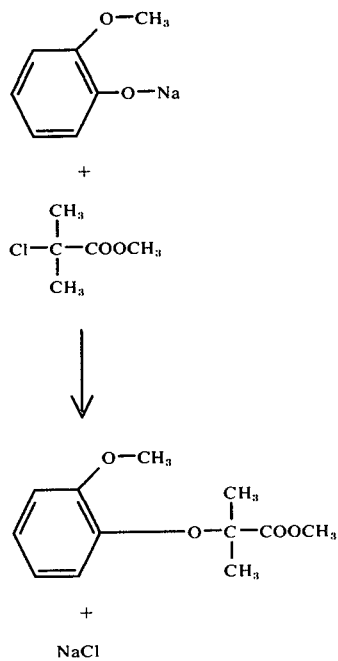

The reaction proceeds smoothly with heating and the product is recovered in the conventional way. The methyl ester is used for preparing the corresponding phosphonate as discussed above.

Alternatively, the phosphonate is prepared from an aliphatic acyl halide and the anion of a dialkyl methylphosphonate. Thus, 2-methyl-2-phenoxypropionyl chloride and dimethyl methylphosphonate yield dimethyl 2-oxo-3-methyl-3-phenoxybutylphosphonate. The acyl halides are readily available from the aliphatic acids by methods known in the art, e.g. chlorides are conveniently prepared using thionyl chloride.

The remaining phosphonates represented by the above formula are conveniently prepared by analogous condensation of the appropriate aliphatic acid ester with a dimethyl methyl phosphonate. For this purpose acids of the general formula $CH_3-(CH_2)_m-C(R_5)_2-COOH$ and cis-$CH_3-CH_2-CH=CH-C(R_5)_2COOH$ are used in the form of their lower alkyl esters, preferably methyl or ethyl.

These acids are known in the art or are available by methods known in the art, for example, by reaction of an appropriate alkenyl or alkyl halide with sodium cyanide to form a nitrile and subsequent hydrolysis to the desired acid.

The formula XXXVIII compound is then prepared from the formula XXXVII compound by reduction of the 3-oxo moiety. This reduction produces either the 3-methyl, 3-methoxy, or 3-hydroxy compound represented by formula XXXVIII.

When the 3-methyl compound is desired, the formula XXXVII compound is methylated with a Grignard reagent of the formula $CH_3MgHal$, where Hal is chloro, bromo, or iodo, followed by hydrolysis of the Grignard complex. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex.

When the 3-hydroxy compound is desired, the reduction of the formula XXXVII compound may be accomplished by use of any of the known ketonic carbonyl reducing agents which do not reduce ester or acid groups or carbon-carbon double bonds, when the latter is undesirable. Examples of these are metal borohydrides, especially sodium, potassium, and zinc borohydride, lithium (tri-tert-butoxy)aluminum hydride, metal trialkoxy borohydrides, e.g., sodium trimethoxy borohydride, lithium borohydride, diisobutylaluminum hydride, and when carbon-carbon double bond reduction is not a problem, the boranes.

When the 3-methoxy compound is desired, the formula XXXVII compound is first reduced to form the 3-hydroxy compound and this 3-hydroxy compound is then etherified by replacing the hydroxy with the -$OCH_3$ moiety. For this purpose, diazomethane may be employed, preferably in the presence of a Lewis acid, e.g., boron trifluoride etherate, aluminum chloride, or fluoboric acid. See Fieser, et al., Reagents for Organic Synthesis, John Wiley and Sons, Inc., New York, New York, (1967), p. 191. The reaction is carried out by mixing a solution of diazomethane in a suitable inert solvent, preferably diethyl ether, with the formula XXXVII compound. Generally the reaction proceeds at about 25° C.

Another method for the alkylation of the 3-hydroxy is by reaction with an alcohol in the presence of boron trifluoride etherate. Thus, methanol and boron trifluoride etherate yield a methyl ether at a reaction temperature of about 25° C. followed conveniently by thin layer chromatography.

Still another method for alkylation of the 3-hydroxy is by the reaction of an alkyl halide e.g. methyl iodide, in the presence of a metal oxide or hydroxide, e.g. barium oxide, silver oxide, or barium hydroxide. An inert solvent may be then added, for example benzene or dimethylformamide. The reactants are preferably stirred together and maintained at temperatures of 25°-75° C.

Still another method for alkylating the 3-hydroxy is first converting the hydroxy to mesyloxy (i.e., methanesulfonate) or tosyloxy (i.e., toluenesulfonate) and thence transforming the mexyloxy or toxyloxy to the -OCH$_3$ moiety by reaction with a metal methoxide, e.g. potassium methoxide. The mesylate or toxylate is prepared by reaction of the formula XXXVII intermediate with either methane-sulfonylchloride or toluenesulfonyl chloride in pyridine. After the mesylate or tosylate is mixed with the appropriate potassium or sodium methoxide in pyridine, the reaction proceeds smoothly at about 25° C. An equivalent amount of the methoxide based on the mesylate is preferred to avoid side reactions.

The above 3-methyl, 3-hydroxy, or 3-methoxy compound is obtained as a 3(RS)-epimeric mixture. The 3(RS)-hydroxy epimers of the formula XXXVIII compound may be appropriately separated using silica gel chromatography. Alternatively, the 3(RS)-hydroxy epimeric mixture may be separated at the point in the process of Chart A, wherein the final prostaglandin type compounds of this invention are prepared as known in the art. Likewise, the 3-methoxy epimers are separated if the 3-hydroxy epimers are separated prior to etherification. The 3-methyl compounds may be separated into their respective epimeric mixtures most advantageously as prostaglandin-type methyl esters.

The formula XXXIX compound is prepared from the formula XXXVIII compound by deacylation with an alkaline metal carbonate, for example, potassium carbonate in methanol at about 25° C. The formula XL compound is then prepared from the formula XXXIX compound by replacement of the free hydroxy moiety or moieties with a blocking group, -OR$_{10}$.

Blocking groups known to the art may likewise be used in this invention. Blocking groups, R$_{10}$, which are useful in this invention, include
1. tetrahydropyranyl;
2. tetrahydrofuranyl; or
3. a group of the formula

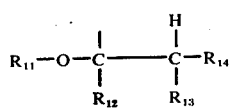

wherein R$_{11}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein R$_{12}$ and R$_{13}$ are the same or different, being hydrogen, alkyl of one to 4 carbon atoms, inclusive, phenyl or phenyl substituted with one, 2, or 3 alkyl of one to 4 carbon atoms, inclusive, or, when R$_{12}$ and R$_{13}$ are taken together -(CH$_2$)$_a$- or -(CH$_2$)$_b$-O-(CH$_2$)$_c$- wherein a is 3, 4, or 5, b is one, 2, or 3, and c is one, 2, or 3 with the proviso that b plus c is 2, 3, or 4, and wherein R$_4$ is hydrogen or phenyl.

When the blocking group R$_{10}$ is tetrahydropyranyl, the tetrahydropyranyl ether is obtained by reaction of the formula XXXIX compound with 2,3-dihydropyran in inert solvent, e.g. dichloromethane, in the presence of an acid condensing agent; such as, p-toluenesulfonic acid or pyridine hydrochloride. The dihydropyran is used in excess, preferably 4 to 10 times the stoichiometric amount. The reaction is normally complete in 15 to 30 min. at 20°-50° C. When the blocking group is tetrahydrofuranyl, 2,3-dihydrofuran is used, instead. When the blocking group is of the formula

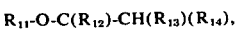

as defined above, the appropriate reagent is a vinyl ether, e.g. isobutyl vinyl ether or any vinyl ether of the formula

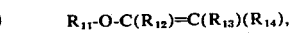

wherein R$_{11}$, R$_{12}$, R$_{13}$, and R$_{14}$ are as defined above; or an unsaturated cyclic or heterocyclic compound e.g. 1-cyclohexen-1-yl methyl ether or 5,6-dihydro-4-methoxy-2-H-pyran. See C. B. Reese, et. al., Journal of the American Chemical Society, 89, 3366 (1967). The reaction conditions for such vinyl ethers and unsaturated compounds are similar to those for dihydropyran above. The formula XLI compound is then prepared by reduction of the formula XL lactone without reducing the ethylenic unsaturation. For this purpose diisobutylaluminum hydride is used. The reduction is done preferably at -60° to -70° C. The formula XLII compound is then prepared from the formula XLI lactol by a Wittig alkylation, using a Wittig reagent derived from the appropriate (ω-carboxyalkyl)triphenylphosphonium bromide,

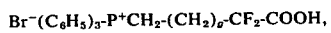

and sodio dimethyl sulfinylcarbanide. The reaction is conveniently carried out at about 25° C. The phosphonium salts used in this Wittig alkylation represent novel compounds of this invention, and their preparation is discussed in the text accompanying Charts D and E hereinafter. The formula XLIII compound is obtained from the formula XLII compound by successively replacing the -OR$_{10}$ groups with free hydroxy moieties; and when R$_7$ is methyl, esterifying the free acid so formed, advantageously with diazomethane, separating the C-15 epimers, where such separation has not been heretofore carried out; followed by a transformation of the carboxy acid ester so formed into the more general R$_1$ moiety.

Hydrolysis of the blocking group is carried out, for example, with methanol-HCl, acetic acid-water-tetrahydrofuran, aqueous citric acid, or aqueous phosphoric acid-tetrahydrofuran, preferably at temperatures below 55° C., thereby avoiding the formation of PGA$_2$-type compounds as by products. When R$_7$ is methyl the free acid so formed is then transformed into its alkyl ester derivative, preferably its methyl ester derivative, in order to achieve effective separation of the C-15 epimers. For this purpose esterification methods discussed hereinbelow may be used. The 15(RS)-epimers are then conveniently separated by silica gel chromatography. Finally, the alkyl ester formed above is transformed to the more general R$_1$ moiety by the methods and procedures discussed hereinbelow.

The formula XLIV compound may also be prepared from the formula XLII compound. The same procedures used in the transformation of the formula XLII into the formula XLIII compound are used, except that before hydrolysis of the blocking groups, the 9-hydroxy group of the formula XLII compound is reduced to form 9-oxo group. This oxidation is preferably performed using the Jones reagent.

The formula XLIV $PGE_2$-type compounds may then be reduced to form either the formula XLV $PGE_1$-type compound or the formula XLVI 13,14-dihydro-$PGE_1$-type compound. Reagents useful for this transformation are known in the art. Thus, hydrogen used at atmospheric pressure or low pressure with catalysts such as palladium-on-charcoal or rhodium-on-aluminum may be advantageously used. See, for example, E. J. Corey, et al., Journal of the American Chemical Society 91, 5677 (1969) and B. Samuelsson, Journal of Biological Chemistry 239, 4091 (1964). For the $PGE_1$-type compounds, the reduction is terminated when one equivalent of hydrogen is absorbed; for the 13,14-dihydro-$PGE_1$-type compounds, 2-equivalents are absorbed. For the $PGE_1$-type compounds it is preferred that a catalyst such as nickel boride be used which selectively effects the reduction of cis-5,6-carbon-carbon double bond in the presence of the trans-13,14-unsaturation. Mixtures of these products are conveniently separated by silica gel chromatography.

The methods described above for the reduction of the $PGE_2$-type compounds to form the corresponding $PGE_1$- and 13,14-dihydro-$PGE_1$-type compounds may be used to form the $PGF_{1\alpha}$ and 13,14-dihydro-$PGF_{1\alpha}$ -type compounds of this invention from the corresponding $PGF_{2\alpha}$ -type compound of formula XLIII.

In Chart B, there is shown an alternate method whereby the $PGF_{2\alpha}$ -type compounds of this invention may be transformed into the corresponding PGE-type compounds of this invention. This method is known in the art. See for example U.S. Pat. No. 3,822,303. The formula XLVIII compound of Chart B is prepared from the formula XLVII compound by a selective silylation of the C-11 and C-15 hydroxy over the C-9 hydroxy of the formula XXXVII compound. Then by methods known in the art, for example, using the procedures of Chart A, the 9-hydroxy group is oxidized to form a 9-oxo group. The formula L compound is then prepared from this formula XLIX compound by hydrolysis of the silyl groups by methods known in the art, for example, the use of water and a water-miscible solvent such as ethanol with acetic acid at ambient temperatures for 2 to 6 hours. These silylation agents are prepared as known in the art. See for reference Post, Silicones and Other Organic Silicone Compounds, Reinhold Publishing Company N. Y., N. Y. (1949). Silylation procedures are likewise known in the art. See for reference Pierce, "Silylation of Organic Compounds," Pierce Chemical Company, Rockford, Illinois (1968).

Chart C shows the transformations from the formula LI PGE-type compounds to corresponding PGF-, PGA-, and PGB-type compounds. In Chart C ~ represents attachment of the hydroxy in either the alpha or the beta position.

The $PGF_\beta$-type compounds of formula LII are prepared by carbonyl, reduction of the PGE-type compounds of formula LI. These carbonyl reductions are carried out by methods known in the art for ring carbonyl reductions of known prostanoic acid derivatives. See, for example Bergstrom, et al. Arkiv, Kemi, 19, 563 (1963), Acta. Chem. Scand. 16,969 (1962), and British Specification No. 1,097,533. Any reducing agent is used which does not react with carbon-carbon double bonds or ester groups. Preferred reagents are lithium (tri-tert-butoxy) aluminum hydride, the metal borohydrides, especially sodium potassium and zinc borohydrides, the metal trialkoxy borohydrides, e.g., sodium trimethoxyborohydrides. The mixtures of alpha and beta hydroxy reduction products are separated into the individual $PGF_\alpha$ - and $PGF_\beta$ -epimers by methods known in the art for separation of analogous paris of C-9 epimers of prostanoic acid derivatives. See, for example Bergstrom, et al. cited above, Granstrom, et al. Journal of Biological Chemistry 240, 457 (1965), and Green, et al., Journal of Lipid Research 5, 117 (1964). Especially preferred separation methods are partitioned chromatographic procedures both normal and reverse phase, preparative thin layer chromatography, and counter-current distribution procedures.

The various PGA-type compounds encompassed by formula LIII are prepared by acidic dehydration of a corresponding PGE-type compound of formula LI. These acidic dehydrations are carried out by procedures known in the art for acidic dehydrations of known prostanoic acid derivatives. See, for example, Pike, et al., Proceedings of the Nobel Symposium II, Stockholm (1966), Interscience Publishers New York pg. 162-163 (1967), and British Specifications 1,097,533. Alkanoic acids of 2-6 carbon atoms, inclusive, especially acetic acid, are preferred acids for this acidic dehydration.

Dilute aqueous solutions of mineral acids, e.g., hydrochloric acid, especially in the presence of a solubilizing diluent, e.g., tetrahydrofuran, are also used for reagents for this acidic dehydration, although these reagents may cause partial hydrolysis of an ester reactant.

The various PGB-type compounds encompassed by formula LIV are prepared by basic dehydration of the corresponding PGE-type compounds encompassed by formula LI or by contacting the corresponding PGA-type compounds encompassed by formula LIII with base. These basic dehydrations and double bond migrations are carried out by methods known in the art for similar reactions of known prostanoic acid derivatives. See, for example, Bergstrom, et al., Journal of Biological Chemistry, 238, 3555 (1963). The base is any whose aqueous solution has pH greater than 10. Preferred bases are alkali metal hydroxides. A mixture of water and sufficient water-miscible alkanol to give a homogeneous reaction mixture is suitable as a reaction medium. The PGE- or PGA-type compound is maintained in such reactive medium until no further PGB-type compound is formed, as shown by the characteristic ultraviolet light absorption near 278 m$\mu$ for the PGB-type compound.

Optically active compounds are obtained from optically active intermediates according to the process steps of Charts A, B and C. When racemic compounds are used in reactions corresponding to the processes in Charts A, B, and C and racemic products are obtained. These racemic products may be used in their racemic form or if preferred may be resolved as optically active isomers by procedures known in the art.

The stereochemistry at C-15 is not altered by the transformations of Charts A and B and C. The 15-epi products of the prostaglandin-type compounds are obtained from 15-epi reactants. Another method of preparing these 15-epi products is by isomerization of the PGF$_1$- or PGE$_1$- type compounds having a 15α-epimeric configuration, by methods known in the art. See, for example, Pike, et al., Journal of Organic Chemistry 34, 3552 (1969).

Charts D and E provide two methods whereby the novel phosphonium intermediates of this invention are advantageously prepared. With reference to Chart B the straight chain ω-bromo alkanoic acids of formula LX are known in the art or may be prepared by methods known in the art. The formula LXI aldehyde may be prepared from the formula LX acid by methods known in the art. For example, the formula LXacid may be reduced to its corresponding primary alcohol using lithium aluminum hydride, and the resulting alcohol then oxidized to form the formula LXI aldehyde by heating with base in aqueous potassium permanganate.

The formula LXII cyanohydrin is then formed by methods known in the art, for example, using aqueous sodium cyanide, or by sulfite addition reaction.

The formula LXIII α-hydroxy alkanoic acid is then formed by methods known in the art. For example, hydrolysis under acidic conditions in a dimethylsulfoxide solvent at reflux temperature may be advantageously used.

Thereafter the formula LXIV α-keto alkanoic acid is formed by oxidation of the formula LXIII compound by methods known in the art. For this purpose the Jones reagent may be advantageously used.

The formula LXV ester, preferably the methyl ester wherein R$_{18}$ is methyl, may be then prepared from the formula LXIV compound preferably using the silver salt esterification method as described hereinbelow. The formula LXVI ω-bromo alpha difluoro alkanoic acid ester is then prepared by fluorination reacting molybdenum hexafluoride and boron trifluoride with the formula LXVI alpha keto alkanoic acid ester. This reaction is advantageously carried out in a methylene chloride solvent with reaction temperatures of below −35° C.

The formula LXVII free acid is then prepared by saponification of the formula LXVI methyl ester.

Saponification, such as is used for saponification of the PGF-type esters of this invention, may be advantageously employed.

Chart E provides a convenient method whereby ω-bromo alpha difluoro acid with a chain length of 5 carbon atoms, may be advantageously prepared. When a prostaglandin-type compound of this invention with the same carboxy chain length as the natural prostaglandins is desired the method of this chart provides the appropriate acid from which the necessary Wittig reagent, described in Chart A, may be prepared.

The formula LXVIII compound, methyl furoate, is known in the art, or may be prepared by methods known in the art. For the purposes of this Chart it is conveniently used in methyl ester form, wherein R$_{18}$ is methyl. The formula LXIX tetrahydro derivative is prepared from the formula LXVIII compound by catalytic hydrogenation. For example, a palladium-on-charcoal catalyst may be advantageously used. The formula LXX compound is then prepared by opening the heterocyclic ring of the formula LXIX compound using an acid bromide of the formula R$_{19}$-COBr. These acid bromides are known in the art or may be prepared by methods known in the art, for example, by reaction of the acid anhydride with anhydrous HBr. For these purposes it is preferred that R$_{19}$ be methyl.

The formula LXXI compound is then prepared from the formula LXX compound by hydrolysis of the alpha acyl group, using, for example, acidic conditions as is known in the art. The formula LXXII compound is then prepared by oxidation of the formula LXXI alpha hydroxy ester. This oxidation is advantageously performed using the Jones reagent. The formula LXIII is then prepared by fluorination of the formula LXXII compound. For this purpose molybdenum hexafluoride and boron trifluoride are used as described above.

Finally the formula LXXIV compound is prepared from the formula LXXIII compound by saponification of the alkyl ester, as described above.

The Wittis reagent is then prepared from either the formula LXVII or the formula LXXIV compound by reaction with triphenylphosphine. Accordingly, there is prepared the triphenylphosphonium salt of the formula:

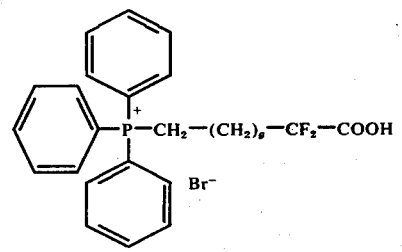

wherein g is 2 to 4, inclusive,

As discussed above, the processes herein described inclusive, lead variously to acids or to esters.

When the alkyl ester has been obtained and an acid is desired, saponification procedures, as known in the art for F-type prostaglandin may be used.

For alkyl esters of E-type prostaglandins enzymatic processes for transformation of esters to their acid forms may be used by methods known in the art. See for reference E. G. Daniels, Process for Producing An Esterase, U.S. Pat. No. 3,761,356.

When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester pufified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods know in the art. See, for example, Organic Reactions, John Wiley and Sons, Inc., New York, N.Y., Vol. 8, pp. 389–394 (1954).

An alternative method for esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Wiley and Sons, Inc., New York (1967). The PG compound is contacted with one to ten molar equivalents of the phenol in the presence of 2-10 molar equivalents of dicyclohexylcarbodiimide in pyridine as a solvent.

The preferred novel process for the preparation of these esters, however, comprises the steps (1) forming a mixed anhydride with the PG compound and isobutylchloroformate in the presence of a tertiary amine and (2) reacting the anhydride with an appropriate phenol or naphthol.

The mixed anhydride is represented by the formula:

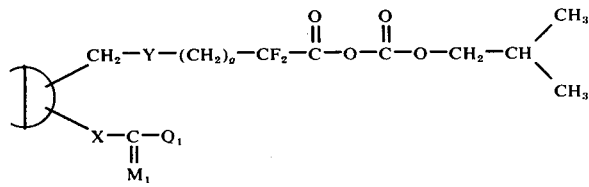

Various methods are available for preparing the phenyl substituted phenyl, as well as the following esters of this invention:

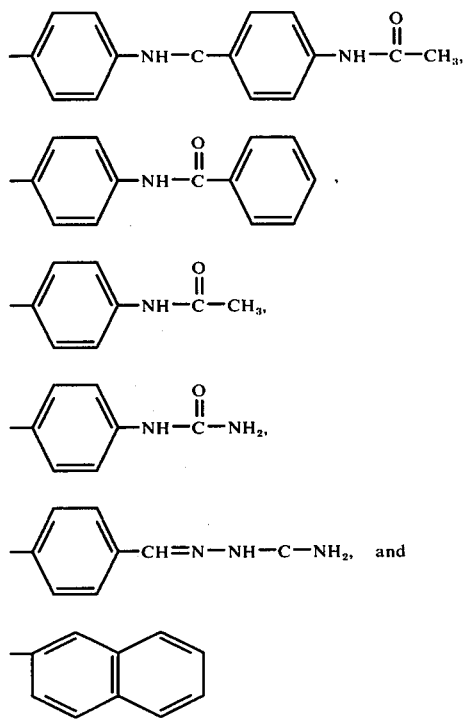

from corresponding phenols or naphthol and the free acid PG compounds differing as to yield and purity of product.

Thus by one method, the PG compound is converted to a tertiary amine salt, reacted with pivaloyl halide to give the mixed acid anhydride and then reacted with the phenol. Alternatively, instead of pivaloyl halide, an alkyl or phenylsulfonyl halide is used, such as p-toluenesulfonyl chloride. See, for example, Belgian patents 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231–236, John for the optically active PG compounds, wherein $\mathfrak{D}$, X, Y, g, $M_1$, and $Q_1$ are as defined above.

The anhydride is formed readily at temperatures in the range −40° to +60° C., preferably at −10° to +10° C. so that the rate is reasonably fast and yet side reactions are minimized. The isobutylchloroformate reagent is preferably used in excess, for example 1.2 molar equivalents up to 4.0 per mole of the PG compound. The reaction is preferably done in a solvent and for this purpose acetone is preferred, although other relatively non-polar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The phenol is preferably used in equivalent amounts or in excess to insure that all of the mixed anhydride is converted to ester. Excess phenol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they may be used, 2-methylpyridine and quinoline result in a slow reaction. A highly hindered amine such as 2,6-dimethyllutidine is not useful because of the slowness of the reaction.

The reaction with the anhydride proceeds smoothly at room temperature (about 20° to 30° C.) and can be followed in the conventional manner with thin layer chromatography.

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium slats. The choice of procedure depends in part upon the solubility characteristics of the particular slat to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. If is preferred to use stoichiometric amounts of the less volatile amines.

Salts whrein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of the formula I to XXXV hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent or solvent, as available in the art, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24 hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography or crystallization.

DESCRIPTION OF THE PREFERRED EMBODIMENTS

The invention can be more fully understood by the following examples and preparations:

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60 spectrophotometer on deuterochloroform solutions with tetramethylsilane as an internal standard.

Mass spectra are recorded on an Atlas CH-4 mass spectrometer with a TO-4 source (ionization voltage 70 ev).

The collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

"Skellysolve-B" SSB refers to mixed isomeric hexanes.

Silica gel chromatography, as used herein, is understood to include elution, collection of fractions, and combination of those fractions shown by TLC (thin layer chromatography) to contain the desired product free of starting material and impurities.

MP (melting points) are determined on a Fisher-Johns melting point apparatus.

DDQ refers to 2,3-dichloro-5,6-dicyano-1,4-benzoquinone.

THF refers to tetrahydrofuran. Preparation 1 3α-Benzoyloxy-5α-hydroxy-2β-(3-oxo-4-phenoxytrans-1-butenyl)-1α-cyclopentaneacetic Acid, γ-Lactone (Formula XXXVII: $R_5$ is hydrogen, $R_9$ is benzoyl, and $Q_1$ is

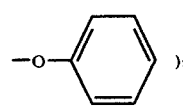

Refer to Chart A.

A. There is first prepared dimethyl 3-phenoxyacetonylphosphonate. A solution of dimethyl methylphosphonate (75 g.) in 700 ml. of tetrahydrofuran is cooled to −75° C. under nitrogen and n-butyllithium (400 ml. of 1.6 molar solution in hexane) is added, keeping the temperature below −55° C. The mixture is stirred for 10 min. and to it is slowly added 2-phenoxyacetyl chloride (44 g.), again keeping the temperature below −55° C. The reaction mixture is stirred at −75° C. for 2 hr., then at about 25° C. for 16 hr. The mixture is acidified with acetic acid and concentrated under reduced pressure. The residue is partitioned between diethyl ether and water, and the organic phase is dried and concentrated to the above-named intermediate, 82 g. Further purification by silica gel chromatography yields an analytical sample having NMR absorptions at 7.4-6.7 (multiplet), 4.78 (singlet), 4.8 and 4.6 (two singlets), and 3.4-3.04 (doublet) δ.

B. The phosphonate anion (ylid) is then prepared as follows. dimethyl 3-phenoxyacetonylphosphonate (step A, 9.3 g.) is added in portions to a cold (5° C.) sodium hydride (1.75 g.) in 250 ml. of tetrahydrofuran, and the resulting mixture is stirred for 1.5 hr. at about 25° C.

C. To the mixture of step B is added the cold solution of the formula XXXVI 3α-benzoyloxy-2β-carboxaldehyde-5α-hydroxy-1α-1-cyclopentaneacetic acid, γ-lactone and the resulting mixture is stirred about 1.6 hr. Then 3 ml. of acetic acid is added and the mixture is concentrated under reduced pressure. A solution is prepared from the residue in 500 ml. of ethyl acetate, washed with several portions of water and brine, and concentrated under reduced pressure. The residue is subjected to silica gel chromatography, eluting with ethyl acetate-Skellysolve B (isomeric hexanes) (3:1). Those fractions shown by TLC to be free of starting material and impurities are combined and concentrated to yield the title compound, 1.7 g. NMR peaks are observed at 5.0-8.2 and 4.7 (singlet) δ.

Following the procedure of Preparation 1, but replacing the optically active formula XXXVI aldehyde with the racemic aldehyde there is obtained the racemic 3-oxo-4-phenoxy-1-butenyl compound corresponding to formula XXXVI.

Following the procedure of Preparation 1, but replacing 2-phenoxyacetyl chloride with each of the following acid esters:

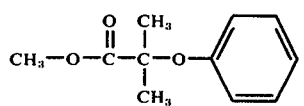

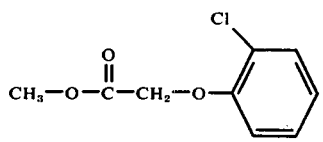

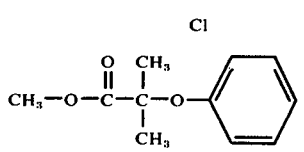

-continued

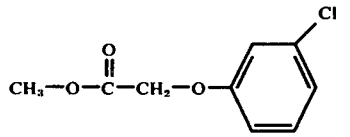

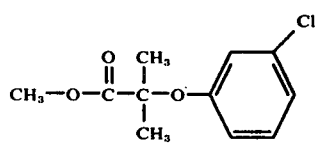

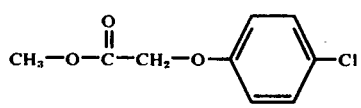

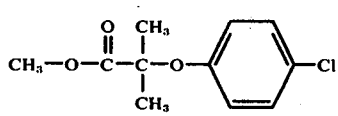

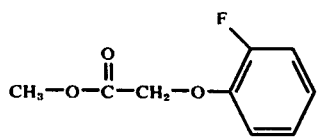

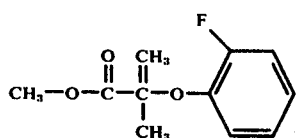

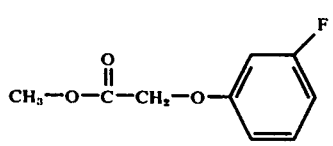

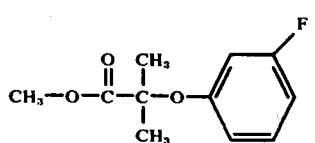

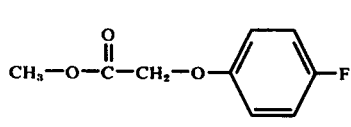

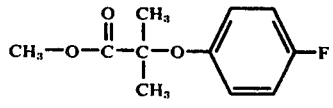

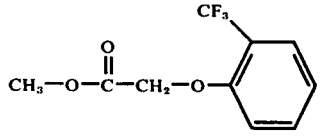

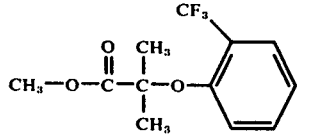

-continued
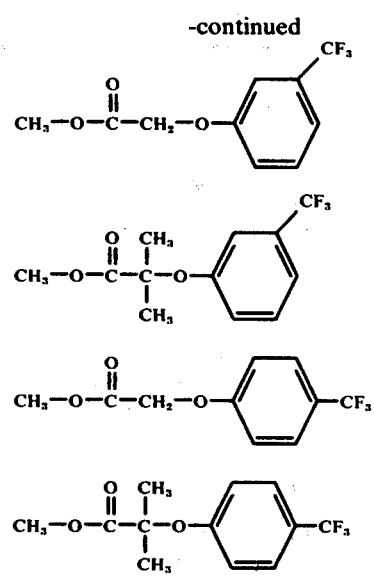
there are respectively obtained the corresponding phosphonates:
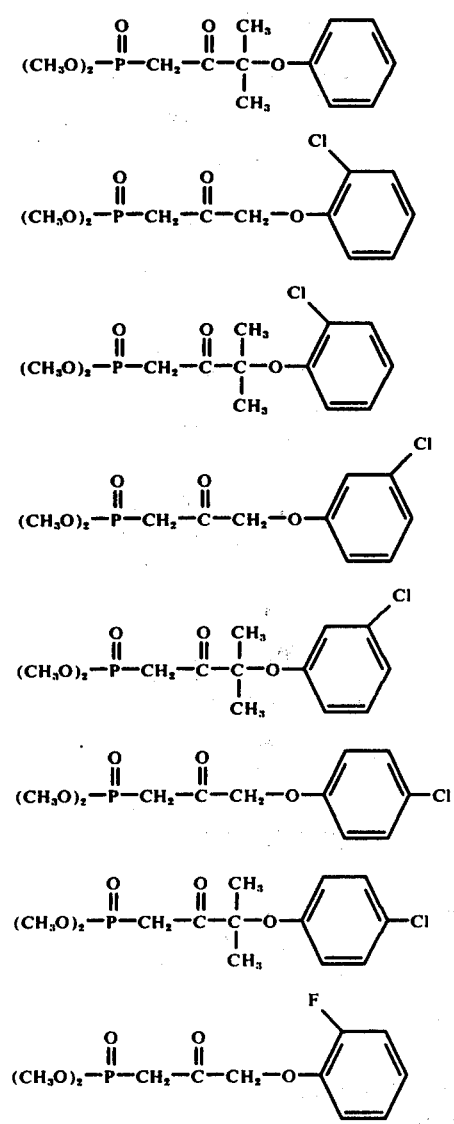
-continued
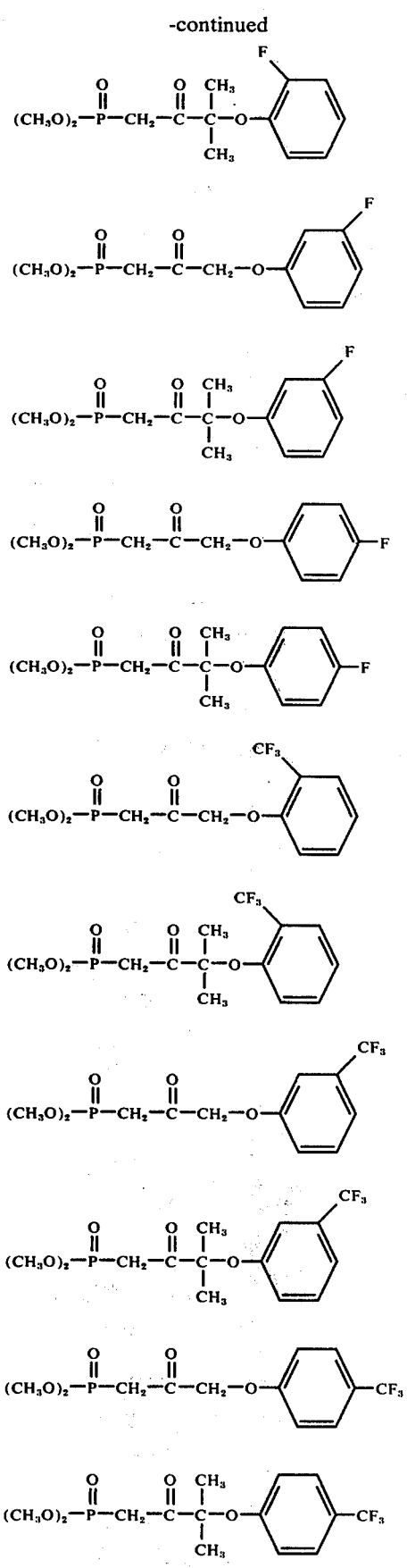
and thereafter the formula-XXXVII lactones:

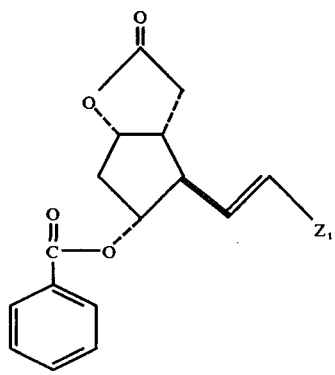

wherein $Z_1$ is:

| Preparation Number | $Z_1$ |
|---|---|
| 2 | -C(=O)-C(CH₃)₂-O-C₆H₅ |
| 3 | -C(=O)-CH₂-O-(2-Cl-C₆H₄) |
| 4 | -C(=O)-C(CH₃)₂-O-(2-Cl-C₆H₄) |
| 5 | -C(=O)-CH₂-O-(3-Cl-C₆H₄) |
| 6 | -C(=O)-C(CH₃)₂-O-(3-Cl-C₆H₄) |
| 7 | -C(=O)-CH₂-O-(4-Cl-C₆H₄) |
| 8 | -C(=O)-C(CH₃)₂-O-(4-Cl-C₆H₄) |
| 9 | -C(=O)-CH₂-O-(2-F-C₆H₄) |
| 10 | -C(=O)-C(CH₃)₂-O-(2-F-C₆H₄) |
| 11 | -C(=O)-CH₂-O-(3-F-C₆H₄) |
| 12 | -C(=O)-C(CH₃)₂-O-(3-F-C₆H₄) |
| 13 | -C(=O)-CH₂-O-(4-F-C₆H₄) |
| 14 | -C(=O)-C(CH₃)₂-O-(4-F-C₆H₄) |
| 15 | -C(=O)-CH₂-O-(2-CF₃-C₆H₄) |
| 16 | -C(=O)-C(CH₃)₂-O-(2-CF₃-C₆H₄) |
| 17 | -C(=O)-CH₂-O-(3-CF₃-C₆H₄) |
| 18 | -C(=O)-C(CH₃)₂-O-(3-CF₃-C₆H₄) |
| 19 | -C(=O)-CH₂-O-(4-CF₃-C₆H₄) |
| 20 | -C(=O)-C(CH₃)₂-O-(4-CF₃-C₆H₄) |

Preparation 21 Dimethyl(2-oxo-3,3-dimethylheptyl)-phosphonate,

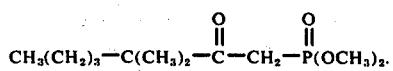

Butyllithium (400 ml.) is slowly added to a solution of dimethylmethylphosphonate (73.7 g.) in 1.3 l. of THF at about −66° C. To the mixture is added a solution of ethyl-2,2-dimethylhexanoate (53 g.) and 150 ml. of THF. The resulting mixture is stirred at −70° C. for 2 hr. Then 46 ml. of acetic acid is added and the mixture is concentrated under reduced pressure. The residue is mixed with portions of difluoromethane (about 1.2 l.) and water (about 150 ml.), shaken and separated. The organic phase is dried over magnesium sulfate and concentrated. Distillation yields the title compound, 41.6 g., boiling point 117°–120° C. Preparation 22 Dimethyl(2-oxohepty)phosphonate,

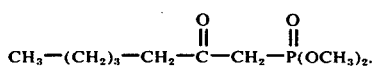

Following the procedure of Preparation 21, but using ethyl hexanoate in place of the ethyl 2,2-dimethyl hexanoate used in Preparation 21, the compound of this preparation is prepared. Preparation 23 Dimethyl(2-oxo-3,3-difluoroheptyl)phosphonate,

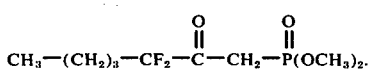

Following the procedure of Preparation 21, but using in place of the ethyl-2,2-dimethyl hexanoate of Preparation 21, ethyl 2,2-difluoro hexanoate, the title compound of this preparation is prepared. Preparation 24 Dimethyl(2-oxo-cis-4-heptenyl)phosphonate,

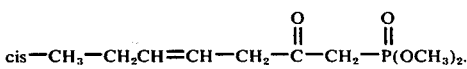

Following the procedure of Preparation 21, but using methyl-cis-3-hexenoate in place of ethyl 2,2-dimethyl hexanoate of Preparation 21, the compound of this preparation is prepared.

The methyl cis-3-hexenoate is prepared from cis-4-1,2-heptendiol, $CH_2(OH)-CH(OH)-CH_2-CH=CH-CH_2-CH_3$, as follows:

0.4 g. of cis-4-1,2-heptenediol (Corey, Journal of the American Chemical Society 93, 1491 (1971)) added to a solution of 100 ml. of ethyl acetate is reacted at ambient temperature with a slight stoichiometric excess of sodium periodate ($NaIO_4$) in aqueous solution. When the reaction is complete, as shown by thin layer chromatography, the organic phase is separted, washed and concentrated under vacuum.

The above product, cis-3-hexenol, is then oxidized in a stoichiometric amount of aqueous potassium permanganate ($KMnO_4$) at ambient temperature The free acid, cis-3-hexenoic acid, is then regenerated from the potassium salt so formed, by addition of dilute hydrochloric acid. The methyl ester thereof is prepared by reaction of the free acid with diazomethane. Preparation 25 Dimethyl (2-oxo-3,3-dimethyl-cis-4-hept phosphonate,

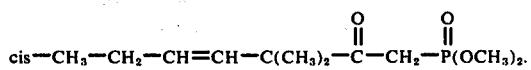

Following the procedure of Preparation 21, but using ethyl 2,2-dimethyl-cis-3-hexenoate in place of the ethyl 2,2-dimethyl hexanoate of Preparation 21, the compound of this preparation is prepared.

The preparation of methyl cis-3-2,2-dimethyl-hexenoate proceeds as follows:

2-Chloro-2-methylpropanol is dissolved in a substantial stoichiometric excess of 2,3-dihydropyran at ambient temperature with stirring. When the reaction is complete, as determined by thin layer chromatography, the THP ether is recovered. This ether is then reacted with sodium ethyl acetylide in aqueous solution. The organic phase is then separated, and hydrogenated using one equivalent of hydrogen over a Lindlar catalyst (palladium), so as to effect the cis-specific reduction. Upon recovery the above ether is hydrolyzed to its free hydroxy by reaction with aqueous acetic acid in a tetrahydrofuran solvent, at 40° C. until the reaction is complete, as shown by thin layer chromatographic methods. The primary alkanol is then treated with aqueous potassium permanganate with heating, thereby forming the potassium salt of the corresponding alkenoic acid. The free acid is then generated by reaction of this potassium salt with dilute hydrochloric acid. The final methyl ester compound is then prepared by reaction of the above acid with diazomethane under the usual conditions. Preparation 26 Dimethyl-2-oxo-3,3-dimethyl-cis-4-heptenyl phosphate,

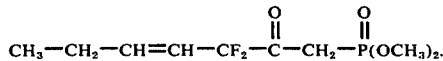

Following the procedure of Preparation 21, but using methyl cis-3-2,2-difluoro-hexenoate in place of the ethyl-2,2-dimethyl hexanoate -dihydropyran Preparation 21 the compound of this preparation is prepared. The methyl cis-3-2,2-difluorohexenoate is prepared as follows:

2-Oxo-3,4-dihydroxy butyric acid is reacted with diazomethane to form the methyl ester. The ester is then reacted with 2,3-dihydropyan in large stoichiometric excess to form the bis(tetrahydropyranyl) ether, the reaction being complete as shown by thin layer chromatography.

This 2-oxo compound is then transformed into a 2,2-difluoro compound by reaction with molybdenum hexafluoride and boron trifluoride, under a dry nitrogen atmosphere, at −78° C. This 2,2-difluoro compound is then subjected to reduction by lithium aluminum hydride forming the corresponding primary alcohol. Upon recovery, this alcohol is then oxidized to the corresponding aldehyde using a Jones reagent, under the usual conditions.

A Wittig alkylation using propyl phosphonium bromide and sodium hydroxide at 0° C. is then carried out in dimethyl sulfoxide.

Hydrolysis of the bis(tetrahydropyranyl) ether moieties then proceeds by reaction with dilute acetic acid. The diol thus formed is then treated successively with sodium periodide, potassium permanganate, and diazomethane following the procedure discussed in Preparation 24. Accordingly, the final methyl ester is prepared.

Preparation 27 3α-Benzoyloxy-5α-hydroxy-2β-(3-oxo-4,4-dimethyl-trans-1-octenyl)-1α-cyclopentaneacetic acid, γ-Lactone (Formula XXXVII: $R_5$ is methyl, $R_9$ is benzoyl, and $Q_1$ is n-butyl).

Following the procedure of parts B and C of Preparation 1, but using dimethyl-2-oxo-3,3-dimethylheptyl phosphonate in place of dimethyl-3-phenoxyacetonyl phosphonate, the compound of this preparation is prepared.

Likewise the following 3α-benzoyloxy-5α-hydroxy-1α-cyclopentaneacetic acid γ-lactones are prepared from the respective dimethyl phosphonates of Preparations 22-26:

| Preparation Number | 3α-Benzoyloxy-5α-hydroxy-1α-cyclopentaneacetic acid, γ-Lactone |
|---|---|
| 28 | 2β-(3-oxo-trans-1-octenyl) |
| 29 | 2β-(3-oxo-4,4-difluoro-trans-1-octenyl) |
| 30 | 2β-(3-oxo-trans-1-cis-5-octadienyl) |
| 31 | 2β-(3-oxo-4,4-dimethyl-trans-1-cis-5-octadienyl) |
| 32 | 2β-(3-oxo-4,4-difluoro-trans-cis-5-octenyl) |

Preparation 33 3α-Benzoyloxy-5α-hydroxy-2β(3α-hydroxy-4-phenoxy-trans-1-butenyl)-1α-cyclopentaneacetic Acid, γ-Lactone (Formula XXXVIII: $R_9$ is benzoyl, $M_2$ is

and $R_5$ is hydrogen, and $Q_1$ is

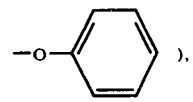

or the 3β-hydroxy epimer (Formula XXXVIII; $R_9$ is benzoyl and $M_2$ is

and $R_5$ is hydrogen, and $Q_1$ is

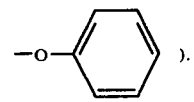

Refer to Chart B. A solution containing ketone-XXXVII (Preparation 1, 2.7 g.) in 14 ml. of 1,2-dimethoxyethane is added to a mixture of zinc borohydride, prepared from zinc chloride (anhydrous, 4.9 g.) in sodium borohydride (1.1 g.) in 48 ml. of dry 1,2-dimethoxyethane, with stirring and cooling to −10° C. Stirring is continued for 2 hr. at 0° C., and water (7.8 ml.) is cautiously added, followed by 52 ml. of ethyl acetate. The mixture is filtered, and the filtrate is separated. The ethyl acetate solution is washed with brine, dried over sodium sulfate, and concentrated under reduced pressure to a mixture of the corresponding formula XXXVIII alpha and beta isomers. The isomers are chromatographed on silica gel, eluting with ethyl acetate, to separate the alpha and beta isomers of the formula XXXVIII compounds.

Following the procedures of Preparation 33, but using the ketones of formula XXXVIII which are shown in Preparations 1-20 and 27-32, the following optically active lactones are obtained:

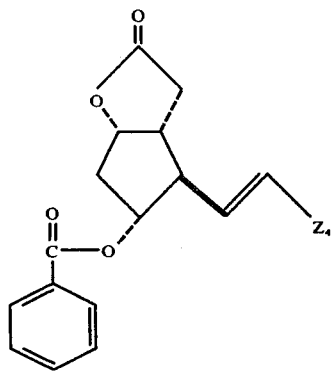

wherein $Z_4$ is:

| Preparation Number | $Z_4$ |
|---|---|
| 34 | −C(=M₂)−C(CH₃)(CH₃)−O−C₆H₅ |
| 35 | −C(=M₂)−CH₂−O−(2-Cl-C₆H₄) |
| 36 | −C(=M₂)−C(CH₃)(CH₃)−O−(2-Cl-C₆H₄) |
| 37 | −C(M₂)−CH₂−O−(2-Cl-C₆H₄) |
| 38 | −C(=M₂)−C(CH₃)(CH₃)−O−(3-Cl-C₆H₄) |
| 39 | −C(=M₂)−CH₂−O−(4-Cl-C₆H₄) |
| 40 | −C(=M₂)−C(CH₃)(CH₃)−O−(4-Cl-C₆H₄) |

-continued

| Preparation Number | $Z_4$ |
|---|---|
| 53 | $-\underset{\underset{M_2}{\|}}{\overset{\underset{\|}{CH_3}}{C}}-\underset{\underset{CH_3}{\|}}{\overset{\|}{C}}-(CH_2)_3-CH_3$ |
| 54 | $-\underset{\underset{M_2}{\|}}{\overset{\|}{C}}-CH_2-(CH_2)_3-CH_3$ |
| 55 | $-\underset{\underset{M_2}{\|}}{\overset{\|}{C}}-CF_2-(CH_2)_3-CH_3$ |
| 56 | cis$-\underset{\underset{M_2}{\|}}{\overset{\|}{C}}-CH_2-CH=CH-CH_2-CH_3$ |
| 57 | cis$-\underset{\underset{M_2}{\|}}{\overset{\underset{\|}{CH_3}}{C}}-\underset{\underset{CH_3}{\|}}{\overset{\|}{C}}-CH=CH-CH_2-CH_3$ |
| 58 | cis$-\underset{\underset{M_2}{\|}}{\overset{\|}{C}}-CF_2-CH=CH-CH_2-CH_3$ | wherein $M_2$ is either

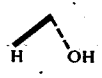

or

Preparation 59 3α-Benzoyloxy-5α-hydroxy-2β-[3-hydroxy-(3RS)-3-methyl-4-phenoxy-trans-1-butenyl]-1α-cyclopentaneacetic Acid, γ-Lactone (Formula XXXVIII: $R_9$ is benzoyl, $Q_1$ is n-butyl, $R_5$ is hydrogen, and $M_2$ is

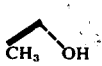

and the 3β-hydroxy epimer (Formula XXXVIII: $R_9$ is benzoyl, $Q_1$ is n-butyl, $R_5$ is hydrogen and $M_2$ is

To a stirred solution of 1.0 g. of 3α-benzoyloxy5α-hydroxy-2β-(3-oxo-4-phenoxy-trans-1-butenyl)-1α-cyclopentaneacetic acid, γ-lactone in 75 ml. of tetrahydrofuran at −78° C. under nitrogen is added dropwise 15 ml. of an ethereal solution 3M in methyl magnesium bromide. The solution becomes heterogeneous. After two hr. a TLC (50 percent ethyl acetate-Skellysolve B) of an aliquot quenched with ether-ammonium chloride shows the reaction to be complete. To the mixture at −78° C. is added dropwise 15 ml. of saturated aqueous ammonium chloride. The resulting mixture is allowed to warm with stirring to ambient temperatures. The mixture is then diluted with diethyl ether and water, equilibrated, and separated. The aqueous layer is extracted three times more with diethyl ether. The organic extracts are combined, washed with brine, dried over sodium sulfate, and evaporated to give the product.

Following the procedure of Preparation 59, but using formula XXXVII lactones described above in Preparations 3, 5, 7, 9, 11, 13, 15, 17, 19, 22, and 24 respectively, there are obtained the lactones of the formula

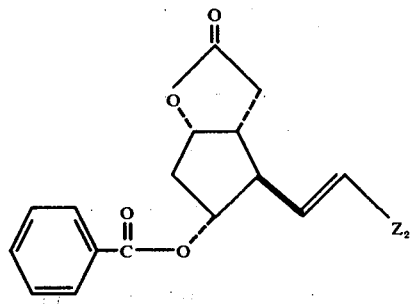

wherein $Z_2$ is respectively.

| Preparation Number | $Z_2$ |
|---|---|
| 60 | 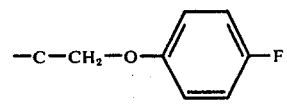 |
| 61 | 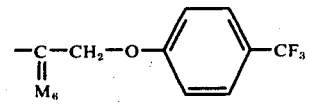 |
| 62 | 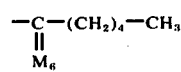 |
| 63 | 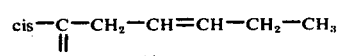 |
| 64 |  |
| 65 |  |
| 66 |  |

-continued

| Preparation Number | $Z_2$ |
|---|---|
| 67 | —C—CH$_2$—O—⟨⟩—F<br>‖<br>M$_6$ |
| 68 | —C—CH$_2$—O—⟨⟩—CF$_3$<br>‖<br>M$_6$ |
| 69 | —C—(CH$_2$)$_4$—CH$_3$<br>‖<br>M$_6$ |
| 70 | cis—C—CH$_2$—CH=CH—CH$_2$—CH$_3$<br>‖<br>M$_6$ | wherein $M_6$ is a mixture of $$\underset{CH_3 \quad OH}{\diagup\!\!\!\diagdown}$$

and $$\underset{CH_3 \quad OH}{\diagup\!\!\!\diagdown}$$

Following the procedure of Preparation 59, but using a racemic lactone described following Preparation 1–20, there are obtained corresponding racemic 3-methyl products. Preparation 71 3α-Benzoyloxy-5α-hydroxy-2β-(3α-methoxy-4-phenoxy-trans-1-butenyl)-1α-cyclopentaneacetic Acid, γ-Lactone (Formula XXXVIII: $R_5$ is hydrogen, $M_2$ is $$\underset{H \quad OCH_3}{\diagup\!\!\!\diagdown},$$

$Q_1$ is n-butyl, and $R_9$ is benzoyl) or its 3β-methoxy epimer (Formula XXXVIII: $R_5$ is hydrogen, $M_5$ is $$\underset{H \quad OCH_3}{\diagup\!\!\!\diagdown}$$

$Q_1$ is n-butyl, and $R_9$ is benzoyl).

Refer to Chart A. A mixture of the formula XXXVIII alpha hydroxy compound (Preparation 33, 2.0 g.) or the beta hydroxy epimer, silver oxide (4.0 g.), and 50 ml. of methyl iodide is stirred and heated at reflux for 68 hr. The mixture is cooled and filtered, and the filtrate concentrated to an oil, 2.0 g. Separation by silica gel chromatography, eluting with 35 percent ethyl acetate in Skelly-solve B and combining those fractions shown by TLC to contain the product free of starting material and impurities, yields the formula XXXVIII title compound as an oil.

Following the procedures of Preparation 71, and using selected hydroxy compounds of Preparations 34–58, as starting material, each is transformed to its corresponding methyl ether compound:

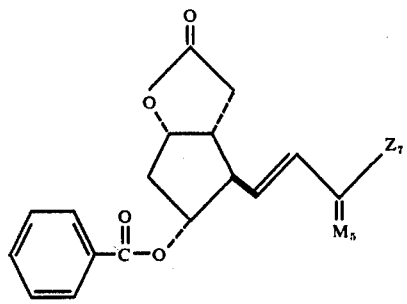

wherein $Z_7$ is as follows:

| Preparation Number | $Z_7$ |
|---|---|
| 72 | -CH₂-O-(2-Cl-C₆H₄) |
| 73 | -CH₂-O-(3-Cl-C₆H₄) |
| 74 | -CH₂-O-(4-Cl-C₆H₄) |
| 75 | -CH₂-O-(2-F-C₆H₄) |
| 76 | -CH₂-O-(3-F-C₆H₄) |
| 77 | -CH₂-O-(4-F-C₆H₄) |
| 78 | -CH₂-O-(2-CF₃-C₆H₄) |
| 79 | -CH₂-O-(3-CF₃-C₆H₄) |
| 80 | -CH₂-O-(4-CF₃-C₆H₄) |
| 81 | -(CH₂)₄-CH₃ |

-continued

| Preparation Number | $Z_7$ |
|---|---|
| 82 | cis-CH₂-CH=CH-CH₂-CH₃ | wherein $M_5$ is

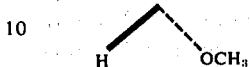

or

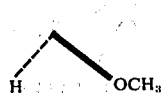

Preparation 83  3α,5α-Dihydroxy-2β-[3α-hydroxy-3-methyl-(3RS)-4-phenoxytrans-1-butenyl]-1α-cyclopentaneacetaldehyde, γ-Lactol, Bis(tetrahydropyranyl) Ether (Formula XLI: $R_5$ is hydrogen, $M_3$ is

$Q_1$ is

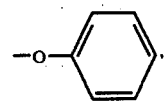

∼ is α or β, and $R_{10}$ THP) or the 3β-hydroxy epimer (Formula XLI: $M_3$ is

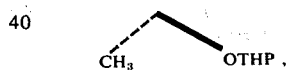

and $R_5$, Q, ∼, and $R_{10}$ are as defined above herein).

A. With reference to Chart B, the formual XXXVIII compound (the compound of Preparation 60, 1.3 g.) in 22 ml. of anhydrous methanol is stirred with potassium carbonate (0.48 g.) for one hr. at about 25° C. and 15 ml. of chloroform is added and the solvent removed under reduced pressure. A solution of the residue in 70 ml. of chloroform is shaken with 10 ml. of warer containing potassium hydrogen sulfate (0.5 g.), then with the brine, and concentrated. The residue is washed with several portions of Skellysolve B (isomeric hexanes) and dried to yield the formula XXXIX compound, 3α,5α-dihydroxy-2β-[(3RS)-3-hydroxy-3-methyl-4-phenoxy-trans-1-butenyl]-1α-cyclopentaneacetic acid, γ-lactone, 0.4 g., which is then used without further purification, below.

B. The formula XXXIX compound from part A above is converted to the formula XL bis(tetrahydropyranyl) ether by reaction with 0.8 ml. of dihydropyran in 10 ml. of dichloromethane in the presence of pyridine hydrochloride (about 0.03 g.). In about 2.5 hr. the mixture is filtered and concentrated to the formula XL product, 0.6 g.

C. The title compound is prepared as follows. Diisobutylaluminumhydride (4.8 ml. of a 10 percent solution in toluene) is added dropwise to a stirred solution of the above formula XL bis(tetrahydropyranyl) ether from part B above in 8 ml. of toluene cooled to −78° C. Stirring is continued at −78° C. for 0.5 hr. whereupon a solution of 3 ml. of tetrahydrofuran and 1 ml. of water is added cautiously. After the mixture warms to 25° C. it is filtered and the filtrate is washed with brine, dried, and concentrated forming mixed alpha and beta hydroxy isomers of the title compounds.

Following the procedure of Preparation 83, each of the optically active compounds described in Preparations 59–70 is transferred to an optically active or racemic compound corresponding to formula XL. There are thus obtained either 3α- or 3β-hydroxy isomers.

Further, using the various formula XXXVIII intermediates provided in Preparations 60–70 there are prepared, following the procedures of Preparation 83, the following formula XLI compounds:

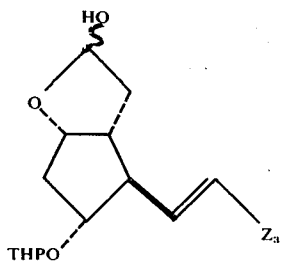

wherein ~ is alpha or beta and $Z_3$ is as follows:

| Preparation Number | $Z_3$ |
|---|---|
| 84 | 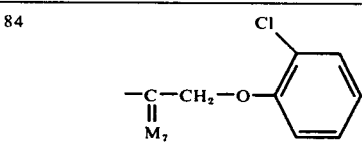 |
| 85 | 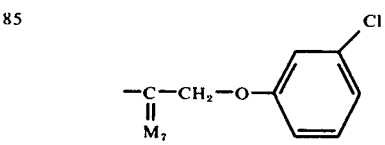 |
| 86 | 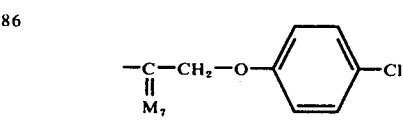 |
| 87 | 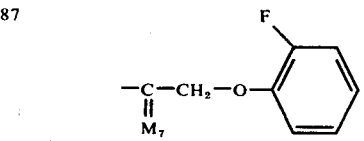 |
| 88 | 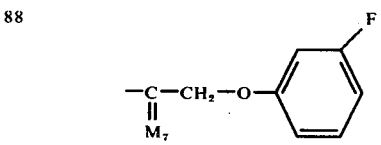 |
| 89 | 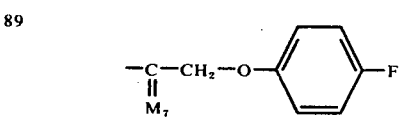 |

| Preparation Number | $Z_3$ |
|---|---|
| 90 |  |
| 91 | 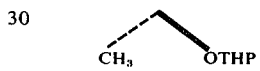 |
| 92 | -C(=M_7)-CH_2-O-C_6H_4-CF_3 | wherein $M_7$ is a mixture of

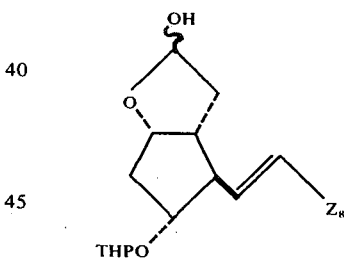

and (CH_3, OTHP structure)

Following the procedures of Preparation 83, using the 4,4-dimethyl and 4,4-difluoro lactones of Preparation 33–58 there are obtained the lactols:

(lactol structure with OH, O, THPO, Z_8)

wherein $Z_8$ is respectively:

| Preparation Number | $Z_8$ |
|---|---|
| 95 | -C(=M_8)-CH_2-O-C_6H_5 |
| 96 | -C(=M_8)(CH_3)-C(CH_3)-O-C_6H_5 |
| 97 | -C(=M_8)-CH_2-O-C_6H_4-Cl |

-continued

| Preparation Number | $Z_8$ |
|---|---|
| 98 | -C(=M_8)-C(CH_3)(CH_3)-O-(2-Cl-C_6H_4) |
| 99 | -C(=M_8)-CH_2-O-(3-Cl-C_6H_4) |
| 100 | -C(=M_8)-C(CH_3)(CH_3)-O-(3-Cl-C_6H_4) |
| 101 | -C(=M_8)-CH_2-O-(4-Cl-C_6H_4) |
| 102 | -C(=M_8)-C(CH_3)(CH_3)-O-(4-Cl-C_6H_4) |
| 103 | -C(=M_8)-CH_2-O-(2-F-C_6H_4) |
| 104 | -C(=M_8)-C(CH_3)(CH_3)-O-(2-F-C_6H_4) |
| 105 | -C(=M_8)-CH_2-O-(3-F-C_6H_4) |
| 106 | -C(=M_8)-C(CH_3)(CH_3)-O-(3-F-C_6H_4) |
| 107 | -C(=M_8)-CH_2-O-(4-F-C_6H_4) |
| 108 | -C(=M_8)-C(CH_3)(CH_3)-O-(4-F-C_6H_4) |

-continued

| Preparation Number | $Z_8$ |
|---|---|
| 109 | -C(=M_8)-CH_2-O-(2-CF_3-C_6H_4) |
| 110 | -C(=M_8)-C(CH_3)(CH_3)-O-(2-CF_3-C_6H_4) |
| 111 | -C(=M_8)-CH_2-O-(3-CF_3-C_6H_4) |
| 112 | -C(=M_8)-C(CH_3)(CH_3)-O-(3-CF_3-C_6H_4) |
| 113 | -C(=M_8)-CH_2-O-(4-CF_3-C_6H_4) |
| 114 | -C(=M_8)-C(CH_3)(CH_3)-O-(4-CF_3-C_6H_4) |
| 115 | -C(=M_8)-C(CH_3)(CH_3)-(CH_2)_3-CH_3 |
| 116 | -C(=M_8)-CF_2-(CH_2)_3-CH_3 |
| 117 | cis-C(=M_8)-CH_2-CH=CH-CH_2-CH_3 |
| 118 | cis-C(=M_8)-C-CH=CH-CH_2-CH_3 |
| 119 | cis-C(=M_8)-CF_2-CH=CH-CH_2-CH_3 | wherein $M_8$ is either

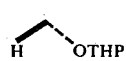

or

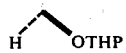

Preparation 120 3α,5α-Dihydroxy-2β-(3α-methoxy-4-phenoxy-trans-1-butenyl-)-1α-cyclopentaneacetaldehyde, γ-Lactol, Tetrahydropyranyl Ether (Formula XL: $R_5$ is hydrogen, $M_3$ is

$Q_1$ is

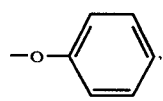

~ is alpha or beta, and $R_{10}$ is THP) and its 3β-methoxy epimer (Formula XL: $M_3$ is

$Q_1$ is

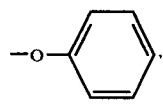

~ is alpha or beta, and $R_{10}$ is THP).
Refer to Chart A.

A. The formula XXXVIII benzoyloxy compound (1.9 g.) and anhydrous potassium carbonate (.68 g.) in 25 ml. of dry methanol is stirred for one hour with extraction of moisture. Chloroform (25 ml.) is added and the mixture is filtered. The filtrate is concentrated to an oil which is taken up in chloroform (50 ml.). The solution is washed with brine, dried over magnesium sulfate, and concentrated to an oil. Separation by silica gel chromatography, eluting with 40:60 ethyl acetate-SSB and combining these fractions shown by TLC to contain the product free from starting material and impurities, yields the deacylated compound.

B. The tetrahydropyranyl (THP) ether is prepared as follows:

A mixture of the compound from part A above (2.35 g.), dihydropyran (3.5 g.), and p-toluenesulfonic acid (about 0.01 g) in 150 ml. of dichloromethane is stirred for 30 minutes. The mixture is washed twice sodium carbonate (10 percent) solution, and brine, and dried over magnesium sulfate. Concentration under reduced pressure yields the THP ether.

C. The formulation XL lactol is prepared as follows:

To the solution of the above (Part B) THP ether in 150 ml. of dry toluene is added with stirring, protected from air with nitrogen, a solution of 105 ml. of diisobutylaluminum hydride (10 percent in toluene) for about 35 min. at about −65° C. Stirring is continued for 30 min. with cooling. The cooling bath is removed, and the mixture of 48 ml. of tetrahydrofuran (THF) and 29 of water is added dropwise over 20 min. The mixture is filtered and the filtrate is washed with brine and dried over magnesium sulfate. Concentration under reduced pressure yields the title compound.

Following the procedure of Preparation 120, but using as starting materials the compounds selected from Preparation 72–82 there are prepared the 3α- or 3β-methoxy lactols:

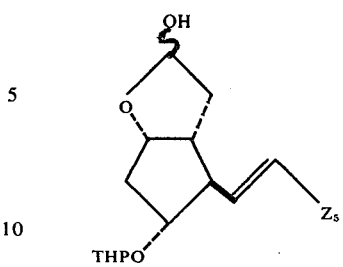

wherein $Z_5$ is respectively:

| Preparation Number | $Z_5$ |
|---|---|
| 121 | -CH_2-O-C_6H_4-Cl (ortho)) |
| 122 | -C(=$M_5$)-CH$_2$-O-C$_6$H$_4$-Cl (ortho) |
| 123 | -C(=$M_5$)-CH$_2$-O-C$_6$H$_4$-Cl (para) |
| 124 | -C(=$M_5$)-CH$_2$-O-C$_6$H$_4$-F (ortho) |
| 125 | -C(=$M_5$)-CH$_2$-O-C$_6$H$_4$-F (meta) |
| 126 | -C(=$M_5$)-CH$_2$-O-C$_6$H$_4$-F (para) |
| 127 | -C(=$M_5$)-CH$_2$-O-C$_6$H$_4$-CF$_3$ (ortho) |
| 128 | -C(=$M_5$)-CH$_2$-O-C$_6$H$_4$-CF$_3$ (meta) |
| 129 | -C(=$M_5$)-CH$_2$-O-C$_6$H$_4$-CF$_3$ (para) |
| 130 | -(CH$_2$)$_4$-CH$_3$ |

| Preparation Number | $Z_5$ |
|---|---|
| 131 | cis-CH$_2$—CH=CH—CH$_2$—CH$_3$ | wherein M$_5$ is

or

EXAMPLE A (4-carboxy-3,3-difluorobutyl)triphenylphosphonium bromide, Br (C$_6$H$_5$)$_3$P-(CH$_2$)$_2$-CH$_2$-CF$_2$-COOH.

50.4 g. of methyl furoate are dissolved in 180 ml. of methanol. Then, 1 g. of 5 percent palladium-on-charcoal is added. The mixture is hydrogenated at 1–3 atmospheres. After 45 hr. 0.8 moles of hydrogen are consumed. The black mixture is filtered using 50 ml. of methanol. Evaporation of the filtrate under reduced pressure at 40°–45° C. yields 51 g. of yellow oil which is then distilled. The fraction boiling at 32°–35° C. at 0.1 mm Hg. is retained.

Anhydrous hydrobromic acid (HBr) is bubbled through 50 ml. of acetic anhydride with cooling until a specific gravity of 1.3 is reached. This reagent is added to 25 g. of the product, methyl tetrahydrofuroate, obtained by distillation above. Moisture is excluded and the mixture is cooled and stirred in an ice bath for 15 min. The mixture is then allowed to stand in ambient temperature for 12 hr. The reaction mixture is then poured into 600 g. of crushed ice and water with stirring. It is extracted 3 times with 250 ml. of diethyl ether. The diethyl ether extract is washed twice with 150 ml. of 5 percent aqueous sodium hydroxide, dried over sodium sulfate, filtered and evaporated under reduced pressure, yielding 38 g. of a pale yellow oil. The oil is distilled under high vacuum. The product collected is at 93°–99° C. (0.2–0.3 mm Hg.) IR absorptions at cm.$^{-1}$ are 1745, 1440, 1375, 1280, 1230, 1155, 1075, and 1050. NMR absorptions of a CDCl$_3$ solution are 1.78–2.2, 2.12, 3.46, 3.73, and 5.0$\delta$.

To a solution of 60 g. of methyl 2-acetoxy-5-bromopentanoate, the compound obtained by the procedure of the preceding paragraph, in 200 ml. of ethanol is added 100 ml. of ice cold methanol saturated with hydrobromic acid. The reaction mixture is allowed to stand at ambient temperature for 12 hr. The solvent is evaporated under reduced pressure at 35° C. bath temperature. 400 ml. of toluene is added and the solvent evaporated again. The residue is dissolved in 200 ml. of ethyl acetate, washed with 400 ml. and 200 ml. of 5 percent aqueous sodium hydroxide and 400 ml. of brine, and dried over sodium sulfate. Filtration and evaporation of solvent under reduced pressure at 45° C. bath temperature yields 42 g. of an oil which is distilled under high vacuum. 28.8 g. of product are obtained. IR absorptions are (cm.$^{-1}$) 3470, 1735, 1440, 1265, 1245, 1220, 1115, and 1095. NMR absorptions in CDCl$_3$ are 1.59 and 2.30, 3.48, 3.78, 4.22, 4.80 $\delta$.

To a solution of 34.4 g. of the compound obtained by the procedure of the preceding paragraph, methyl 2-hydroxy-5-bromopentanoate, in 400 ml. of acetone is added with stirring and cooling in the water bath 75 ml. of Jones reagent (from 26.7 g. of CrO$_3$ in 23 ml. of concentrated sulfuric acid), maintaining the reaction temperature at 30°–40° C. After addition is complete the resulting mixture is stirred for 1.5 hr. 150 ml. of isopropyl alcohol is added, and stirring is continued for 30 min. The reaction mixture is diluted with 1800 ml. of water, extracted with methylene chloride, and washed with brine, and dried with sodium sulfate. Filtration and evaporation under reduced pressure yields 30.8 g. of a pale yellow oil. IR absorptions are observed at 1750, 1730, 1435, 1290, 1265, 1075, and 1055 cm.$^{-1}$.

Under dry nitrogen atmosphere, 195 ml. of molybdenum hexafluoride and boron trifluoride is cooled in a dry ice acetone bath. A solution of the compound obtained in the preceeding paragraph (30.8 g. in 40 ml. of methylene chloride) is added with stirring. Stirring continues for one hr. Thereafter the stirred mixture is diluted with 200 ml. of methylene chloride and 400 ml. of water. The aqueous layer is extracted with methylene chloride and the combined organic extracts are combined washed with water, potassium bicarbonate, and brine. Filtration and evaporation of the solvent yields 31.1 g. of a dark brown oil, which is distilled under high vacuum to 14 g.

Thereafter, 28 g. of methyl 2,2-difluoro-5-bromopentanoate, obtained from the preceeding paragraph, are stirred in 175 ml. of aqueous hydrobromic acid (specific gravity 1.71) for 3 hr. at ambient temperature. The reaction mixture is cooled in an ice bath and diluted with 1300 ml. of diethyl ether. The layers are separated and the aqueous layer is extracted twice with 400 ml. of diethyl ether. The combined ether solutions are washed 3 times with 450 ml. of water, then backwashed with 400 ml. of ether and the combined ether solutions are dried over sodium sulfate. Filtration and evaporation of solvent yields 27.7 g. of a pale yellow oil which is used without further purification. NMR absorptions in CDCl$_3$ at 1.72–2.75, 3.48, and 9.5 $\delta$.

A mixture of 15.2 g. of the compound obtained following the procedure of the above paragraph, 2,2-difluoro-5-bromo pentanoic acid, 80 ml. of acetonitrile and 22 g. of triphenyl phosphine are refluxed with stirring for 30 hr. The reaction mixture is heated to 110° C., and diluted with 160 ml. of toluene. The mixture is allowed to crystallize. The heating is discontinued and the mixture is allowed to cool slowly to ambient temperature with stirring. After 12 hr. the mixture is stored in 5° C. for 24 hr. The precipitate is collected on a filter washed with 50 ml. of toluene and dried under vacuum at ambient temperature. 20.9 g. of the product of this example is obtained. IR absorption (cm.$^{-1}$) at 2760, 2600, 2420, 1750, 1690, 1590, 1575, 1490, 1440, 1205, 1115, 1095, 1060, 1000, 735, 720, and 690. Melting point 165°–173° C. Preparation 132 p-Benzamidophenol

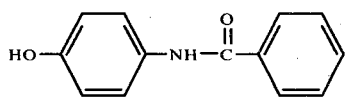

A solution of p-hydroxyaniline (20 g.) in 200 ml. of pyridine is treated with benzoic anhydride (20 g.). After 4 hr. at about 25° C., the mixture is concentrated under reduced pressure and the residue is taken up in 200 ml. of hot methanol and precipitated with 300 ml. of water. The product is recrystallized from hot acetonitrile as white crystals, 8.5 g., melting point 218.0°–218.5° C. Preparation 133 p-(p-Acetamidobenzamido)phenol

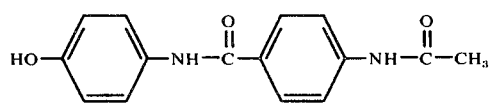

A solution of p-acetamidobenzoic acid (12.5 g.) in 250 ml. of tetrahydrofuran is treated with triethylamine (11.1 ml.). The mixture is then treated with isobutylchloroformate (10.4 ml.) and, after 5 min. at about 25° C., with p-aminophenol (13.3 g.) in 80 ml. of dry pyridine. After 40 min. the crude product is obtained by addition of 2 liters of water. The product is recrystallized from 500 ml. of hot methanol by dilution with 300 ml. of water as white crystals, 5.9 g., melting point 275.0°–277.0° C.

EXAMPLE 1

2,2-Difluoro-16-phenoxy-17,18,19,20,-tetranor-$PGF_{2\alpha}$ (Formula I: g is 2, $R_1$ and $R_5$ are hydrogen, s is 0 and $M_1$ is

or its methyl ester.

Refer to Chart A.

A. The free acid prepared from the lactol of Preparation 95 which is of the same epimeric configuration at the 3 position of its side chain as the desired configuration at C-15 position of the prostaglandin-type product of this example. The reaction of this part is carried out under an atmosphere of nitrogen with exclusion of moisture. 20 ml. of dimethyl sulfoxide is added to 0.88 g. of a 50 percent sodium hydride dispersion in mineral oil. The mixture is stirred and heated at 70° to 80° C. for 1 hour, then cooled in an ice bath. 4.4 g. of the phosphonium salt of Example A, (3,3-difluoro-4-carboxybutyl)triphenylphosphonium bromide, is added with stirring. The ice bath is removed and stirring is continued for 15 min. 2 g. of the lactol of Preparation 95 dissolved in 5 ml. of dimethyl sulfoxide and 5 ml. of benzene is added dropwise, followed by 10 ml. of benzene. Stirring is continued for 1.5 hr. The reaction mixture is then diluted with 200 ml. of benzene and a solution of 3 g. of potassium bisulfate in 75 ml. of water. The layers are separated and the aqueous layer is extracted twice with 100 ml. of benzene. The organic solutions are combined and washed twice with 50 ml. of water. The water is backwashed with 100 ml. of benzene, and the combined benzene solutions are then dried over sodium sulfate. Filtration and evaporation of solvent yields the bis-tetrahydropyranyl ether of 2,2-difluoro-$PGF_{2\alpha}$.

B. When the methyl ester is prepared esterification is accomplished by adding 40 ml. of diazomethane in an ether solution to the product of part A. After 1 hr. at ambient temperature the solvents are evaporated under reduced pressure. The resulting oil is dissolved in 25 ml. of methylene chloride and chromatographed over 200 g. of silica gel, and the title methyl esters are thereby obtained, as bis(tetrahydropyranyl)ethers.

C. Using either the free acid from part A of this example or the methyl ester from part B of this example the tetrahydropyranyl groups are hydrolyzed, as follows, to form the prostaglandin-type product of this example. Either of the above products are heated in 12 ml. of a 20:10:3 acetic-water-tetrahydrofuran mixture at 40 to 45° C for 3 hr. The reaction mixture is then diluted with 12 ml. of water and freeze-dried. The product is then dissolved in 5 ml. of methylene chloride and chromatographed over silica gel.

Thus, the compounds of this example are prepared.

Following the procedure of Example 1 there are prepared either free acid or methyl ester form and with either 15α or 15β configuration, the following prostaglandin-type compounds of this invention, from the indicated lactol starting material:

| Example Number | 2,2-difluoro-$PGF_2\alpha$-type compound | Preparation of Lactol Starting Material |
|---|---|---|
| 2 | 16-methyl-16-phenoxy-18,19,20-trinor | 96 |
| 3 | 16-(o-chlorophenoxy)-17,18,19,20-tetranor | 97 |
| 4 | 16-methyl-16-(o-chlorophenoxy)-18,19,20-trinor | 98 |
| 5 | 16-(m-chlorophenoxy)-17,18,19,20-tetranor | 99 |
| 6 | 16-methyl-16-(m-chlorophenoxy)-18,19,20-trinor | 100 |
| 7 | 16-(p-chlorophenoxy)-17,18,19,20-tetranor | 101 |
| 8 | 16-methyl-16-(p-chlorophenoxy)-18,19,20-trinor | 102 |
| 9 | 16-(o-fluorophenoxy)-17,18,19,20-tetranor | 103 |
| 10 | 16-methyl-16-(o-fluorophenoxy)-18,19,20-trinor | 104 |
| 11 | 16-(m-fluorophenoxy)-17,18,19,20-tetranor | 105 |
| 12 | 16-methyl-16-(m-fluorophenoxy)-18,19,20-trinor | 106 |
| 13 | 16-(p-fluorophenoxy)-17,18,19,20-tetranor | 107 |
| 14 | 16-methyl-16-(p-fluorophenoxy)-18,19,20-trinor | 108 |
| 15 | 16-(o-trifluoromethylphenoxy)-17,18,19,20-tetranor | 109 |
| 16 | 16-methyl-16-(o-trifluoromethylphenoxy)-18,19,20-trinor | 110 |
| 17 | 16-(m-trifluoromethylphenoxy)-17,18,19,20-tetranor | 111 |
| 18 | 16-methyl-16-(m-trifluoromethylphenoxy)-18,19,20-trinor | 112 |
| 19 | 16-(p-trifluoromethylphenoxy)-17,18,19,20-tetranor | 113 |
| 20 | 16-methyl-16-(p-trifluoromethylphenoxy)-18,19,20-trinor | 114 |
| 21 | 16,16-dimethyl | 115 |
| 22 | 16,16-difluoro | 116 |

There are also prepared the following PGF$_{3\alpha}$ -type compounds:

| Example Number | 2,2-difluoro-PGF$_3\alpha$-type compound | Preparation of Lactol Starting Material |
|---|---|---|
| 23 | — | 117 |
| 24 | 16,16-dimethyl | 118 |
| 25 | 16,16-difluoro | 119 |

EXAMPLE 26

2,2-Difluoro-15(S)-15-methyl-PGF$_2\alpha$, Methyl Ester (Formula XVI: wherein g is 2, m is 3, R$_1$ is methyl, R$_5$ is hydrogen, and M$_1$ is

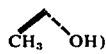

and 2,2-Difluoro-15(R)-15-methyl-PGF$_2\alpha$, Methyl Ester (Formula XVI: wherein g is 2, m is 3, R$_1$ is methyl, R$_5$ is hydrogen and M$_1$ is

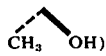

and their corresponding free acids.

Refer to Chart A.

a. The starting material for the preparation of the compounds of this example is the bis-tetrahydropyranyl ether lactol of Preparation 93. This lactol is provided as a mixture of 3$\alpha$ and 3$\alpha$ epimers. Following the procedure of Example 1 Parts A and B using 5 g. of the above lactol and 2.2 g. of a 50 percent sodium hydride dispersion in mineral oil and 11.1 g. of the phosphonium salt of Preparation 132 followed by silica gel chromatography, the 2,2-difluoro-15(R) and (S)-PGF$_2\alpha$ $\alpha$methyl ester 11,15-bis-tetrahydropyranyl ether is prepared. NMR absorptions are observed in CDCl$_3$ at 0.85, 1.03-2.7, 3.18-4.29, 3.85, 4.69, and 5.06-5.80 $\delta$.

B. The 15-epimers of the product of Part A of this example are separated as follows:

A solution of 2.65 g. of the compound of part A of this example and 15 ml. of a 20:10:3 mixture of acetic acid-water-tetrahydrofuran is allowed to stand at ambient temperature for 2.5 hr. The solution is then diluted with 16 ml. of water and lyophilized. The residue is dissolved in 40 ml. of methylene chloride and chromatographed over 400 g. of silica gel. The column is eluted with the following 400 ml. portions: 6 portions of 80 percent methylene chloride, 20 percent acetone, and 19 portions of 70 percent methylene chloride 30 percent acetone. 226 mg. of the 15(R)-epimer are obtained in fractions 12 and 13. 143 mg. of the 15(S)-epimer are obtained in fractions 11 and 14. 104 mg. of a mixture of R and S epimers are obtained in fraction 15. 625 mg. of primarily the 15(R)-epimer and some minor by-products are obtained in fractions 16–23. These 625 mg. are again chromatographed on silica gel. The column is developed with the following 100 ml. portions. 14 portions of 70 percent methylene chloride 30 percent acetone, 13 portions of 60 percent methylene chloride 40 percent acetone. 28 mg. of the 15(S)-epimer is obtained in fractions 9 and 10. 42 mg. of a mixture of 15(R) and 15(S)-epimers are obtained in fractions 11–14. 350 mg. of the 15(R)-epimer are obtained in fractions 15–20. The 15(R)-epimer has IR absorptions at (cm.$^{-1}$) 3380, 1770, 1445, 1355, 1320, 1275, 1215, 1200, 1090, 1035, 975, 830, 785, and 730. The 15(R)-epimer had NMR absorption in CDCl$_3$ at 0.88, 1.25, 2.93, 3.63-4.27, 3.87, 5.07-5.68. The high resolution mass spectrograph of the TMS derivative of the 15(R)-epimer yields a base peak at 634.3716. For the 15(S)-epimer IR absorptions are observed at (cm.$^{-1}$) 3320, 1770, 1320, 1260, 1215, 1200, 1090, 1040, 970, 920, 910, 835, and 735. For the 15(S)-epimer NMR absorptions in CDCl$_3$ at 0.88, 1.05-2.55, 1.29, 3.23, 3.70-4.28, 3.88, 5.05-5.69$\delta$. The mass spectrum of the TMS derivative of the 15(S)-epimer gave the following peaks 637, 619, 563, 544, 529, 463, 454, 447, 217. The high resolution mass spectrograph of the TMS derivative of the 15(S)-epimer showed a base peak at 634.3694.

C. The free acid of each of the epimers obtained in part B of this example are obtained by saponification by reacting the methyl ester with one equivalent of dilute sodium hydroxide in methanolic solution, followed by acidification with dilute methanolic hydrochloric acid.

Following the procedure of Example 26 there are prepared in either free acid or methyl ester form with either the 15(R) or 15(S) configuration the following 2,2-difluoro-15-methyl-PGF$_2\alpha$ -type compounds of this invention from the indicated lactol starting material:

| Example Number | 2,2-difluoro-15-methyl-17,18,19,20-tetranor-PGF$_2\alpha$-type compounds | Preparation of Lactol Starting Material |
|---|---|---|
| 27 | 16-(o-chlorophenoxy) | 84 |
| 28 | 16-(m-chlorophenoxy) | 85 |
| 29 | 16-(p-chlorophenoxy) | 86 |
| 30 | 16-(o-fluorophenoxy) | 87 |
| 31 | 16-(m-fluorophenoxy) | 88 |
| 32 | 16-(p-fluorophenoxy) | 89 |
| 33 | 16-(o-trifluoromethylphenoxy) | 90 |
| 34 | 16-(m-trifluoromethylphenoxy) | 91 |
| 35 | 16-(p-trifluoromethylphenoxy) | 92 |
| 36 | 16-phenoxy | 83 |

Again following the procedure of Example 26 there is prepared 2,2-difluoro-15(S)-15-methyl-PGF$_3\alpha$ methyl ester and free acid and the corresponding 15(R)-epimers from the lactol starting material of Preparation 94.

Following the procedure of Example 26 there are prepared in both methyl ester and free acid form and with either 15(R) or 15(S) configuration the following 2,2-difluoro-PGF$_2\alpha$, 15-methyl ether type compounds of this invention from the indicated lactol starting materials below.

| Example Number | 2,2-difluoro-17,18,19,20-tetranor-PGF$_2\alpha$, 15-methyl ether type compounds | Preparation of Lactol Starting Material |
|---|---|---|
| 37 | 16-phenoxy | 120 |
| 38 | 16-(o-chlorophenoxy) | 121 |
| 39 | 16-(m-chlorophenoxy) | 122 |
| 40 | 16-(p-chlorophenoxy) | 123 |
| 41 | 16-(o-fluorophenoxy) | 124 |
| 42 | 16-(m-fluorophenoxy) | 125 |
| 43 | 16-(p-fluorophenoxy) | 126 |
| 44 | 16-(o-trifluoromethyl- | 127 |

| Example Number | 2,2-difluoro-17,18,19,20-tetranor-PGF$_2\alpha$, 15-methyl ether type compounds | Preparation of Lactol Starting Material |
| --- | --- | --- |
| | phenoxy) | |
| 45 | 16-(m-trifluoromethyl-phenoxy) | 128 |
| 46 | 16-(p-trifluoromethyl-phenoxy) | 129 |
| 47 | — | 130 |

Again following the procedure of Example 26, but using as starting material the lactol of Preparation 131 there is prepared 2,2-difluoro-15(S)-PGF$_3\alpha$, 15-methyl ether in both free acid and methyl ester form and its corresponding 15(R)-epimer.

EXAMPLE 48

2,2-Difluoro-16-phenoxy-17,18,19,20-tetranor-PGE$_2$ (Formula II; g is 2, s is 0, R$_1$ and R$_5$ are hydrogen, and M$_1$ is

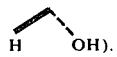

A solution of 0.4 g. of 2,2-difluoro-16-phenoxy-PGF$_2\alpha$ -11,15-bis-tetrahydropyranyl ether in 12 ml. of acetone is cooled to about −20° C. To this solution is added slowly 0.5 ml. of Jones reagent (2.1 g. of chromium trioxide, 6 ml. of water, and 1.7 ml. of concentrated sulfuric acid). The mixture is stirred for 15 min. and then shaken with 30 ml. of ice water and 200 ml. of dichloromethane diethyl ether in a 1 to 3 ratio. The organic phase is washed with cold dilute hydrochloric acid, cold water, and brine. It is then dried and concentrated. The residue is the bis(tetrahydropyranyl)ether of the title compound.

B. A solution of the product of step A of this example in 9.5 ml. of acetic acid and 4.5 ml. of water is stirred at 37°–39° C. for 2.5 hr. The mixture is neutralized with sodium bicarbonate solution, then saturated with salt, and shaken with dichloromethane diethyl ether in a 1 to 3 ratio. It is then dried and concentrated. The residue is chromatographed over silica gel eluting with 25 percent ethyl acetate and Skellysolve B and 0.6 percent methanol in ethyl acetate. The fractions shown by thin layer chromatography to contain the desired product free of starting material and impurities are combined and concentrated to yield the title compound of this example.

Following the procedure of this example and using the 15(R)-epimer of the compound of Example 1 or the methyl ester forms of either the 15(S)- or 15(R)-epimer of Example 1 the corresponding PGE$_2$-type compounds are obtained.

Likewise there are obtained the PGE$_2$ and PGE$_3$-type compounds corresponding to each of the PGF$_2\alpha$ and PGF$_3\alpha$ -type compounds of Examples 2–47, following the procedures of Example 48. Accordingly, Examples 49–96 are provided.

EXAMPLE 97

2,2-Difluoro-16-phenoxy-17,18,19,20-tetranor-PGE$_1$ (formula VI: g is 2, s is 0, R$_1$ and R$_5$ are hydrogen, and M$_1$ is

A mixture of the bis(tetrahydropyranyl) ether of 2,2-difluoro-16-phenoxy-17,18,19,20-tetranor-PGE$_2$, Example 48 part A, 220 mg., 5 percent rhodium-on-alumina catalyst (40 g.) and 16 ml. of ethyl acetate is stirred under 1 atmosphere of hydrogen at 0° C. until substantially all of the starting material has been used, as shown by thin layer chromatography. The mixture is filtered to remove the catalyst and the filtrate is concentrated. The residue is dissolved in 1 ml. of tetrahydrofuran and 6 ml. of 66 percent acetic acid. The mixture is then warmed to 50° C. for 2.5 hr. The mixture is concentrated under reduced pressure and the residue is chromatographed over silica gel, eluting with the upper layer of a mixture of ethyl acetate-acetic acid-Skellysolve B-water (90:20:50:100). Those fractions shown by thin layer chromatography to contain the title compound free of starting material and impurities are combined and concentrated to yield the title compounds.

Following the procedure of Example 97, but using as starting material the PGE$_2$-type compounds of the preceding examples, there are obtained the corresponding 2,2-difluoro-PGE$_1$-type compounds of this invention. Accordingly, Examples 98–142 are provided.

EXAMPLE 143

2,2-Difluoro-16-phenoxy-17,18,19,20-tetranor-13,14-dihydro-PGE$_1$ (Formula XII: wherein g is 2, s is 0, R$_1$ and R$_5$ are hydrogen, and M is

A solution of 2,2-difluoro-16-phenoxy-17,18,19,20-tetranor-PGE$_2$ (Example 48, 100 mg.) in 10 ml. of ethyl acetate is shaken with hydrogen at about 1 atmosphere of pressure at 25° C. in the presence of a 5 percent palladium-on-charcoal catalyst (15 mg.). Two equivalents of hydrogen are used, whereupon the hydrogenation is stopped and the catalyst is removed by filtration. The filtrate is concentrated under reduced pressure and the residue is chromatographed on silica gel eluting with ethyl acetate Skellysolve B ranging from 50 to 100 percent ethyl acetate. Those fractions shown by thin layer chromatography to contain the desired product free of starting material and impurities are combined and concentrated to give the title compound.

Following the procedure of Example 143, but using as starting materials the PGE$_2$ compounds described hereinabove there are obtained the corresponding 2,2-difluoro-13,14-dihydro-PGE$_1$-type compounds of this invention. Accordingly, there are provided Examples 144–188.

EXAMPLE 189

2,2-Difluoro-16-phenoxy-17,18,19,20-tetranor-PGA$_2$ (Formula III: wherein g is 2, s is 0, R$_1$ and R$_5$ are hydrogen, and M$_1$ is

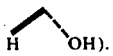

Refer to Chart C.

A solution of 2,2-difluoro-16-phenoxy-17,18,19,20-tetranor-PGE$_2$ methyl ester (Example 48, 300 mg.), 4 ml. of tetrahydrofuran and 4 ml. of 0.5 N. hydrochloric acid is left standing at 25° C. for 5 days. Brine and dichloromethane ether (1:3) are added and the mixture stirred. The organic phase is separated, dried, and concentrated. The residue is dissolved in diethyl ether and the solution is extracted with saturated aqueous sodium bicarbonate. The aqueous phase is acidified with dilute hydrochloric acid and then extracted with dichloromethane. This extract is dried and concentrated to yield the title compound.

Following the procedure of Example 189 each of the 2,2-difluoro-PGE-type compounds of this invention is transformed into the corresponding PGA-type compounds of this invention.

EXAMPLE 190

2,2-Difluoro-16-phenoxy-17,18,19,20-tetranor-PGB$_2$ (Formula IV: wherein g is 2, s is 0, R$_1$ and R$_5$ are hydrogen and M$_1$ is

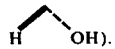

Refer to Chart C.

A solution of 2,2-difluoro-16-phenoxy-17,18,19,20-tetranor-PGE$_2$ methyl ester (Example 48, 200 mg.) in 100 ml. of 50 percent aqueous ethanol containing about 1 g. of potassium hydroxide is kept at 25° C. for 10 hr. under nitrogen. The solution is then cooled to 10° C. and neutralized with the addition of 3 N hydrochloric acid at 10° C. The resulting solution is extracted repeatedly with ethyl acetate, and the combined ethyl acetate extracts are washed with water and then brine, dried, and concentrated to yield the title compound.

Following the procedure of Example 190, but using in place of the PGE$_2$-type compound of that example the PGE$_2$-type compound of that example the PGE-type compounds of Examples 49-188, there are obtained the corresponding PGB-type compounds.

EXAMPLE 191

2,2-Difluoro-16-phenoxy-17,18,19,20-tetranor-PGF$_2\beta$ (Formula V: g is 2, s is 0, R$_1$ and R$_5$ are hydrogen, M$_1$ is

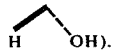

and its 9$\alpha$-isomer (Formula I: g is 2, s is 0, R$_1$ and R$_5$ are hydrogen, M$_1$ is

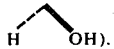

Refer to Chart C.

A solution of sodium borohydride 300 mg. in 6 ml. of ice cold methanol is added to a solution of 2,2-difluoro-16-phenoxy-17,18,19,20-tetranor-PGE$_2$ (Example 6, 650 mg.) in 30 ml. of methanol at −5° C. The mixture is stirred for an additional 5 min., made slightly acidic with acetic acid and concentrated under reduced pressure. The residue is extracted with dichloromethane and the organic phase is washed with water, dilute aqueous sodium bicarbonate, and brine. It is then dried over sodium sulfate and concentrated under reduced pressure. This residue is chromatographed over silica gel eluting with 1 to 10 percent ethanol in ethyl acetate. Those fractions containing the title compound free of starting material and impurities, as shown by thin layer chromatography, are combined and concentrated to yield the PGF$_{2\beta}$ -type title compounds of this example. In other fractions, the corresponding PGF$_{2\alpha}$ -type compound of this example is obtained.

Following the procedure of Example 191, but using each of the 2,2-difluoro-PGE-type compounds of Examples 49-188, there are obtained the corresponding PGF$\beta$ and PGF$\alpha$ compounds.

EXAMPLE 192

2,2-Difluoro-16-phenoxy-17,18,19,20-tetranor-PGF$_{2\alpha}$, Sodium Salt

A solution of 2,2-difluoro-16-phenoxy-17,18,19,20-tetranor-PGF$_{2\alpha}$ (Example 1, 100 mg.) in 50 ml. of water ethanol mixture (1:1) is cooled to 5° C. and neutralized with an equivalent amount of 0.1 N aqueous sodium hydroxide solution. The neutral solution is concentrated to a residue of the title compound.

Following the procedure of Example 192, but using potassium hydroxide, calcium hydroxide, tetramethyl ammonium hydroxide, benzyl trimethyl ammonium hydroxide, in place of sodium hydroxide, there are obtained the corresponding potassium, calcium tetramethyl ammonium, and benzyl trimethyl ammonium salts of 2,2-difluoro-16-phenoxy-17,18,19,20-tetranor-PGF$_{2\alpha}$.

Likewise following the procedure of Example 17, but using each of the 2,2-difluoro-PG-type compounds of Examples 1-191, and those compounds described in the text following Examples 189, 190, and 191 there are prepared the sodium, potassium, calcium, tetramethyl ammonium, and benzyl trimethyl ammonium salts of these compounds.

EXAMPLE 193 p-Acetamidophenyl Ester of 2,2-Difluoro-16-phenoxy-17,18,19,20-tetranor-PGF$_{2\alpha}$.

A solution of 2,2-difluoro-16-phenoxy-17,18,19,20-tetranor-PGF$_{2\alpha}$ in acetone is treated at −10° C. with twice the stoichiometric amount of trimethylamine as prostaglandin analog and also with an equal quantity of isobutyl chloroformate, whereupon trimethylamine hydrochloride is precipitated. After 5 min. the mixture is treated with several fold stoichiometric excess over the prostaglandin analog of p-acetamidophenol in pyridine for 3 hr. at 25° C. The solvent is removed under reduced pressure and the residue is taken up in acetonitrile and again concentrated. The crude residue is subjected to silica gel chromatography, eluting with ethyl acetate and methanol (ratio 90:1). The residue obtained by concentration of selected fractions is the title compounds of this example. Following the procedure of Example 193, using any of the PG-type free acids of Examples 1–191 or those compounds described in the paragraph following Examples 189–191, and a phenol or naphthol selected from the group consisting of p-acetamidophenol, p-(p-acetamidobenzamido)phenyl, p-benzamidophenol, p-hydroxyphenyl urea, p-hydroxybenzaldehyde semi carbazone, 2-naphthol, the corresponding substituted phenyl or naphthyl esters of these PG-type compounds are obtained.

I claim:
1. A compound of the formula

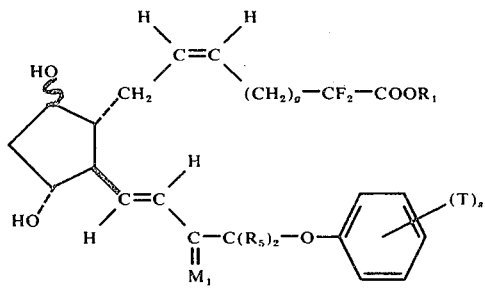

or a mixture comprising that compound and the enantiomer thereof,
wherein g is 2 to 4, inclusive;
wherein $M_1$ is

or

wherein $R_7$ and $R_8$ are hydrogen or methyl, with the proviso that one of $R_7$ or $R_8$ is methyl only when the other is hydrogen;
wherein T is alkyl of one to 3 carbon atoms, inclusive, fluoro, chloro, trifluoromethyl, or $-OR_4$ wherein $R_4$ is alkyl of one to 3 carbon atoms, inclusive, and wherein s is zero, one, 2, or 3, with the proviso that not more than two T's are other than alkyl;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro, alkyl of one to 4 carbon atoms, inclusive, or a pharmacologically acceptable cation.

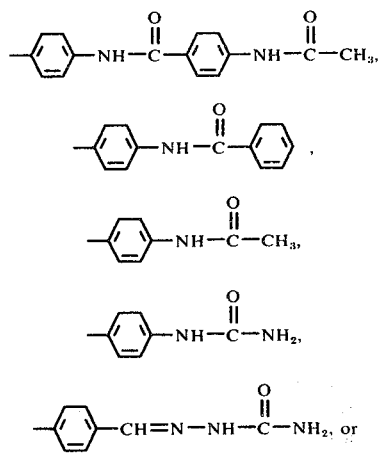

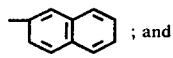

wherein $R_5$ is hydrogen or methyl, with the proviso that $R_5$ is methyl only when $R_7$ and $R_8$ are both hydrogen.

2. A compound according to claim 1, wherein $M_1$ is

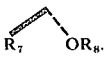

3. A compound according to claim 2, wherein g is 2.
4. A compound according to claim 3, wherein s is 0 or s is one and T is chloro, fluoro, or trifluoromethyl.
5. A compound according to claim 4, wherein $R_7$ is methyl.
6. A compound according to claim 5, wherein s is 1 and T is trifluoromethyl.
7. 2,2-Difluoro-15-methyl-16-(m-trifluoromethylphenoxy)-17,18,19,20-tetranor-PGF$_{2\alpha}$, a compound according to claim 6, wherein $R_1$ is hydrogen.
8. 2,2-Difluoro-15-methyl-16-(m-trifluoromethylphenoxy)-17,18,19,20-tetranor-PGF$_{2\alpha}$, methyl ester, a compound according to claim 6, wherein $R_1$ is methyl.
9. A compound according to claim 5, wherein s is 1 and T is fluoro.
10. 2,2-Difluoro-15-methyl-16-(p-fluorophenoxy)-17,18,19,20-tetranor-PGF$_{2\alpha}$, a compound according to claim 9, wherein $R_1$ is hydrogen.
11. 2,2-Difluoro-15-methyl-16-(p-fluorophenoxy)-17,18,19,20-tetranor-PGF$_{2\alpha}$, methyl ester, a compound according to claim 9, wherein $R_1$ is methyl.
12. A compound according to claim 5, wherein s is one and T is chloro.
13. 2,2-Difluoro-15-methyl-16-(p-chlorophenoxy)-17,18,19,20-tetranor-PGF$_{2\alpha}$, a compound according to claim 12, wherein $R_1$ is hydrogen.
14. 2,2-Difluoro-15-methyl-16-(p-chlorophenoxy)-17,18,19,20-tetranor-PGF$_{2\alpha}$, methyl ester, a compound according to claim 12, wherein $R_1$ is methyl.
15. A compound according to claim 5, wherein s is 0.
16. 2,2-Difluoro-15-methyl-16-phenoxy-17,18,19,20-tetranor-PGF$_{2\alpha}$, a compound according to claim 15, wherein $R_1$ is hydrogen.
17. 2,2-Difluoro-15-methyl-16-phenoxy-17,18,19,20-tetranor-PGF$_{2\alpha}$, methyl ester, a compound according to claim 15, wherein $R_1$ is methyl.
18. A compound according to claim 4, wherein $R_8$ is methyl.
19. A compound according to claim 18, wherein s is one, and T is trifluoromethyl
20. 2,2-Difluoro-16-(m-trifluoromethylphenoxyl)-17,18,19,20-tetranor-PGF$_{2\alpha}$, 15-methyl ether, compound according to claim 19, wherein $R_1$ is hydrogen.
21. 2,2-Difluoro-16-(m-trifluoromethylphenoxy)-17,18,19,20-tetranor-PGF$_{2\alpha}$, 15-methyl ether, methyl ester, a compound according to claim 19, wherein $R_1$ is methyl.
22. A compound according to claim 18, wherein T is fluoro.

23. 2,2-Difluoro-16-(p-fluorophenoxy)-17,18,19,20-tetranor-PGF$_{2\alpha}$, 15-methyl ether, a compound according to claim 22, wherein R$_1$ is hydrogen.

24. 2,2-Difluoro-16-(p-fluorophenoxy)-17,18,19,20-tetranor-PGF$_{2\alpha}$, 15-methyl ether, methyl ester, a compound according to claim 22, wherein R$_1$ is methyl.

25. A compound according to claim 18, wherein s is one and T is chloro.

26. 2,2-Difluoro-16-(p-chlorophenoxy)-17,18,19,20-tetranor-PGF$_{2\alpha}$, 15-methyl ether, methyl ester, a compound according to claim 25, wherein R$_1$ is hydrogen.

27. 2,2-Difluoro-16-(p-chlorophenoxy)-17,18,19,20-tetranor-PGF$_{2\alpha}$, 15-methyl ether, methyl ester, a compound according to claim 25, wherein R$_1$ is methyl.

28. A compound according to claim 18, wherein s is 0.

29. 2,2-Difluoro-16-phenoxy-17,18,19,20-tetranor-PGF$_{2\alpha}$, 15-methyl ether, a compound according to claim 28, wherein R$_1$ is hydrogen.

30. 2,2-Difluoro-16-phenoxy-17,18,19,20-tetranor-PGF$_{2\alpha}$, 15-methyl ether, methyl ester, a compound according to claim 28, wherein R$_1$ is methyl.

31. A compound according to claim 4, wherein R$_7$ and R$_8$ are hydrogen.

32. A compound according to claim 31, wherein R$_5$ is methyl.

33. A compound according to claim 32, wherein s is one and T is trifluoromethyl.

34. 2,2-Difluoro-16-methyl-16-(m-trifluoromethylphenoxy)-18,19,20-trinor-PGF$_{2\alpha}$, a compound according to claim 33 wherein R$_1$ is hydrogen.

35. 2,2-Difluoro-16methyl-16-(m-trifluoromethylphenoxy)-18,19,20-trinor-PGF$_{2\alpha}$, methyl ester, a compound according to claim 33, wherein R$_1$ is methyl.

36. A compound according to claim 32, wherein s is one and T is fluoro.

37. 2,2-difluoro-16-methyl-16-(p-fluorophenoxy)-18,19,20-trinor-PGF$_{2\alpha}$, a compound according to claim 36, wherein R$_1$ is hydrogen.

38. 2,2-Difluoro-16-methyl-16-(p-fluorophenoxy)-18,19,20-trinor-PGF$_{2\alpha}$, methyl ester, a compound according to claim 36, wherein R$_1$ is methyl.

39. A compound according to claim 32, wherein s is one and T is chloro.

40. 2,2-Difluoro-16-methyl-16-(p-chlorophenoxy)-18,19,20-trinor-PGF$_{2\alpha}$, a compound according to claim 39, wherein R$_1$ is hydrogen.

41. 2,2-Difluoro-16-methyl-16-(p-chlorophenoxy)-18,19,20-trinor-PGF$_{2\alpha}$, methyl ester, a compound according to claim 39, wherein R$_1$ is methyl.

42. A compound according to claim 32, wherein s is 0.

43. 2,2-Difluoro-16-methyl-16-phenoxy-18,19,20-trinor-PGF$_{2\alpha}$, methyl ester, a compound according to claim 42, wherein R$_1$ is methyl.

44. 2,2-Difluoro-16-methyl-16-phenoxy-18,19,20-trinor-PGF$_{2\alpha}$, methyl ester, a compound according to claim 42, wherein R$_1$ is methyl.

45. A compound according to claim 31, wherein R$_5$ is hydrogen.

46. A compound according to claim 45, wherein s is one and T is trifluoromethyl.

47. 2,2-Difluoro-16-(m-trifluoromethylphenoxy)-17,18,19,20-tetranor-PGF$_{2\alpha}$, a compound according to claim 46, wherein R$_1$ is hydrogen.

48. 2,2-Difluoro-16-(m-trifluoromethylphenoxy)-17,18,19,20-tetranor-PGF$_{2\alpha}$, methyl ester, a compound according to claim 46, wherein R$_1$ is methyl.

49. A compound according to claim 45, wherein s is one and T is fluoro.

50. 2,2-Difluoro-16-(p-fluorophenoxy)-17,18,19,20-tetranor-PGF$_{2\alpha}$, a compound according to claim 49, wherein R$_1$ is hydrogen.

51. 2,2-Difluoro-16-(p-fluorophenoxy)-17,18,19,20-tetranor-PGF$_{2\alpha}$, methyl ester, a compound according to claim 49, wherein R$_1$ is methyl.

52. A compound according to claim 45, wherein s is one and T is chloro.

53. 2,2-Difluoro-16-(p-chlorophenoxy)-17,18,19,20-tetranor-PGF$_{2\alpha}$, a compound according to claim 49, wherein R$_1$ is hydrogen.

54. 2,2-Difluoro-16-(p-chlorophenoxy)-17,18,19,20-tetranor-PGF$_{2\alpha}$, methyl ester, a compound according to claim 52, wherein R$_1$ is methyl.

55. A compound according to claim 45, wherein s is 0.

56. 2,2-Difluoro-16-phenoxy-17,18,19,20-tetranor-PGF$_{2\alpha}$, a compound according to claim 55, wherein R$_1$ is hydrogen.

57. 2,2-Difluoro-16-phenoxy-17,18,19,20-tetranor-PGF$_{2\alpha}$, methyl ester, a compound according to claim 55, wherein R$_1$ is methyl.

58. The compound according to claim 1, wherein M$_1$ is

* * * * *

UNITED STATES PATENT OFFICE
CERTIFICATE OF CORRECTION

Patent No. 4,001,300                Dated January 4, 1977

Inventor(s) Udo F. Axen

It is certified that error appears in the above-identified patent and that said Letters Patent are hereby corrected as shown below:

Column 1, line 50, that portion of the formula reading

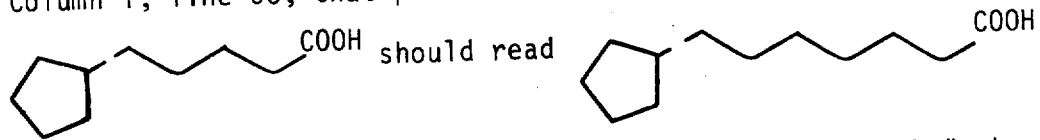

Column 8, line 67, "range 0.01 to 20 µg. of body weight" should read -- range 0.1 to 20 µg. per kg. of body weight --;
Column 11, line 66, that portion of Figure VI reading

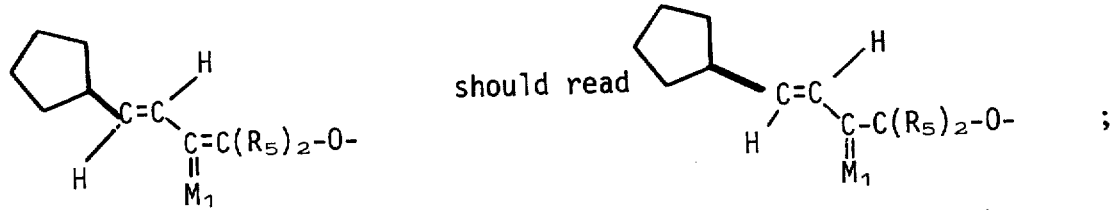

Column 22, line 37, "structure," should read -- structure. --; line 54, "C-2b, C-4, C-5," should read -- C-2b, C-3, C-4, C-5, --;
Column 45, line 17, "toxylate" should read -- tosylate --;
Column 46, line 24, "methoxy-2-H-pyran" should read -- methoxy-2H-pyran --; line 38, "Br-($C_6H_5$)$_3$-P+$CH_2$-" should read -- Br-($C_6H_5$)$_3$-P±$CH_2$- --
Column 47, line 65, "carbonyl," should read -- carbonyl --;
Column 53, line 16, "slat" should read -- salt --;

UNITED STATES PATENT OFFICE
CERTIFICATE OF CORRECTION

Patent No. 4,001,300  Dated January 4, 1977

Inventor(s) Udo F. Axen

It is certified that error appears in the above-identified patent and that said Letters Patent are hereby corrected as shown below:

Column 53, line 37, "If is" should read -- It is --;
Column 62, line 41, "hexanoate -dihydropyran" should read -- hexanoate --;
Column 66, line 55, "3α-benzoyloxy5α" should read -- 3α-benzoyloxy-5α --;
Column 68, line 35, "Preparation" should read -- Preparations --;
Column 70, line 51, "warer" should read -- water --;
Column 75, line 49, "twice sodium" should read -- twice with sodium --; line 53, "formulation XL" should read -- formula XL --; line 61, "and 29 of water" should read -- and 29 ml. of water --;
Column 80, line 11, "obtained, as" should read -- obtained as --; line 17, "acetic-water" should read -- acetic acid-water --; line 60, "fluoro-methylphenoxy-" should read -- fluoromethylphenoxy) --;
Column 81, line 40, "$PGF_{2\alpha}$ amethyl" should read -- $PGF_{2\alpha}$ methyl --;
Column 86, line 35, "calcium tetra-" should read -- calcium, tetra- --;
Column 89, line 36, "16methyl" should read -- 16-methyl --; line 42, "2,2-difluoro" should read -- 2,2-Difluoro --.

Signed and Sealed this

Tenth Day of October 1978

[SEAL]

Attest:

RUTH C. MASON
Attesting Officer

DONALD W. BANNER
Commissioner of Patents and Trademarks